(12) United States Patent
Li et al.

(10) Patent No.: US 7,888,325 B2
(45) Date of Patent: *Feb. 15, 2011

(54) COMPOSITION AND METHOD FOR IN VIVO AND IN VITRO ATTENUATION OF GENE EXPRESSION USING DOUBLE STRANDED RNA

(75) Inventors: Yin-Xiong Li, Augusta, GA (US); Michael J. Farrell, Canoga Park, CA (US); Margaret J. Kirby, Augusta, GA (US)

(73) Assignee: Medical College of Georgia Research Institute, Inc., Augusta, GA (US)

( * ) Notice: Subject to any disclaimer, the term of this patent is extended or adjusted under 35 U.S.C. 154(b) by 1083 days.

This patent is subject to a terminal disclaimer.

(21) Appl. No.: 11/637,623

(22) Filed: Dec. 12, 2006

(65) Prior Publication Data

US 2009/0156520 A1    Jun. 18, 2009

Related U.S. Application Data

(63) Continuation of application No. 10/772,661, filed on Feb. 5, 2004, now abandoned, which is a continuation of application No. 10/038,984, filed on Jan. 4, 2002, which is a continuation of application No. 09/493,301, filed on Jan. 28, 2000, now abandoned.

(60) Provisional application No. 60/117,635, filed on Jan. 28, 1999, provisional application No. 60/175,400, filed on Jan. 11, 2000.

(51) Int. Cl.
*A61K 31/70* (2006.01)
*C07H 21/04* (2006.01)

(52) U.S. Cl. ................................ 514/44; 536/24.5
(58) Field of Classification Search ............... None
See application file for complete search history.

(56) References Cited

U.S. PATENT DOCUMENTS

| | | |
|---|---|---|
| 3,931,397 A | 1/1976 | Harnden |
| 4,130,641 A | 12/1978 | Ts'o et al. |
| 4,283,393 A | 8/1981 | Field et al. |
| 4,469,863 A | 9/1984 | Ts'o et al. |
| 4,605,394 A | 8/1986 | Skurkovich |
| 4,766,072 A | 8/1988 | Jendrisak et al. |
| 4,897,355 A | 1/1990 | Eppstein et al. |
| 5,024,938 A | 6/1991 | Nozaki et al. |
| 5,034,323 A | 7/1991 | Jorgensen et al. |
| 5,107,065 A | 4/1992 | Shewmaker et al. |
| 5,173,410 A | 12/1992 | Ahlquist |
| 5,190,931 A | 3/1993 | Inouye |
| 5,208,149 A | 5/1993 | Inouye |
| 5,231,020 A | 7/1993 | Jorgensen et al. |
| 5,264,618 A | 11/1993 | Felgner et al. |
| 5,272,065 A | 12/1993 | Inouye et al. |
| 5,279,833 A | 1/1994 | Rose |
| 5,283,184 A | 2/1994 | Jorgenson et al. |
| 5,283,185 A | 2/1994 | Epand et al. |
| 5,365,015 A | 11/1994 | Grierson et al. |
| 5,422,241 A | 6/1995 | Goldrick et al. |
| 5,453,566 A | 9/1995 | Shewmaker et al. |
| 5,459,127 A | 10/1995 | Felgner et al. |
| 5,514,546 A | 5/1996 | Kool |
| 5,578,716 A | 11/1996 | Szyf et al. |
| 5,580,859 A | 12/1996 | Felgner et al. |
| 5,583,021 A | 12/1996 | Dougherty et al. |
| 5,624,803 A | 4/1997 | Noonberg et al. |
| 5,631,148 A | 5/1997 | Urdea |
| 5,643,762 A | 7/1997 | Ohshima et al. |
| 5,683,985 A | 11/1997 | Chu et al. |
| 5,693,773 A | 12/1997 | Kandimalla et al. |
| 5,714,323 A | 2/1998 | Ohshima et al. |
| 5,739,309 A | 4/1998 | Dattagupta et al. |
| 5,747,338 A | 5/1998 | Giese et al. |
| 5,795,715 A | 8/1998 | Livache et al. |
| 5,798,265 A | 8/1998 | Springer et al. |
| 5,808,036 A | 9/1998 | Kool |
| 5,814,500 A | 9/1998 | Dietz |
| 5,837,533 A | 11/1998 | Boutin |
| 5,850,026 A | 12/1998 | DeBonte et al. |
| 5,874,555 A | 2/1999 | Dervan et al. |
| 5,908,779 A | 6/1999 | Carmichael et al. |
| 5,922,602 A | 7/1999 | Kumagai et al. |
| 5,932,241 A | 8/1999 | Gorman |
| 5,945,290 A | 8/1999 | Cowsert |
| 5,972,704 A | 10/1999 | Draper et al. |

(Continued)

FOREIGN PATENT DOCUMENTS

AU    199919380    7/1999

(Continued)

OTHER PUBLICATIONS

U.S. Appl. No. 09/646,807, Not Published, Graham et al.

(Continued)

*Primary Examiner*—Tracy Vivlemore
(74) *Attorney, Agent, or Firm*—Mueting Raasch & Gebhardt, P.A.

(57) ABSTRACT

Introduction of double stranded RNA into cells, cell culture, organs and tissues, and whole organisms, particularly vertebrates, specifically attenuates gene expression.

30 Claims, 8 Drawing Sheets

U.S. PATENT DOCUMENTS

| | | |
|---|---|---|
| 5,981,505 A | 11/1999 | Weiner et al. |
| 5,998,383 A | 12/1999 | Wright et al. |
| 6,010,908 A | 1/2000 | Gruenert et al. |
| 6,022,863 A | 2/2000 | Peyman |
| 6,054,299 A | 4/2000 | Conrad |
| 6,127,170 A | 10/2000 | Boutin |
| 6,133,024 A | 10/2000 | Helene et al. |
| 6,217,900 B1 | 4/2001 | Ciccarelli et al. |
| 6,291,504 B1 | 9/2001 | Nugiel et al. |
| 6,369,038 B1 | 4/2002 | Blumenfeld et al. |
| 6,372,965 B1 | 4/2002 | Lightner et al. |
| 6,423,885 B1 | 7/2002 | Waterhouse et al. |
| 6,482,804 B1 | 11/2002 | Musunuri et al. |
| 6,506,559 B1 | 1/2003 | Driver et al. |
| 6,531,647 B1 | 3/2003 | Baulcombe et al. |
| 6,573,099 B2 | 6/2003 | Graham |
| 6,635,805 B1 | 10/2003 | Baulcombe et al. |
| 2002/0086356 A1 | 7/2002 | Tuschl et al. |
| 2002/0114784 A1 | 8/2002 | Li et al. |
| 2002/0132257 A1 | 9/2002 | Giordano et al. |
| 2002/0162126 A1 | 10/2002 | Beach et al. |
| 2002/0168707 A1 | 11/2002 | Graham |
| 2002/0173478 A1 | 11/2002 | Gewirtz et al. |
| 2003/0018993 A1 | 1/2003 | Gutterson et al. |
| 2003/0027783 A1 | 2/2003 | Zernicka-Goetz et al. |
| 2003/0036197 A1 | 2/2003 | Glassman et al. |
| 2003/0051263 A1 | 3/2003 | Fire et al. |
| 2003/0056235 A1 | 3/2003 | Fire et al. |
| 2003/0061626 A1 | 3/2003 | Plaetinck et al. |
| 2003/0074684 A1 | 4/2003 | Graham et al. |
| 2003/0084471 A1 | 5/2003 | Beach et al. |
| 2003/0157030 A1 | 8/2003 | Davis et al. |
| 2003/0159161 A1 | 8/2003 | Graham et al. |
| 2003/0165894 A1 | 9/2003 | Waterhouse et al. |
| 2003/0180756 A1 | 9/2003 | Shi et al. |
| 2003/0228691 A1 | 12/2003 | Lewis et al. |
| 2004/0018999 A1 | 1/2004 | Beach et al. |
| 2004/0022748 A1 | 2/2004 | Ananthapadmanabhan et al. |
| 2004/0029275 A1 | 2/2004 | Brown et al. |
| 2004/0064842 A1 | 4/2004 | Graham et al. |
| 2004/0138168 A1 | 7/2004 | Satishchandran et al. |
| 2004/0180439 A1 | 9/2004 | Graham et al. |
| 2004/0237145 A1 | 11/2004 | Graham et al. |
| 2004/0266005 A1 | 12/2004 | Graham et al. |
| 2005/0250208 A1 | 11/2005 | Graham et al. |
| 2006/0014715 A1 | 1/2006 | Graham et al. |

FOREIGN PATENT DOCUMENTS

| | | |
|---|---|---|
| AU | 199929163 | 10/1999 |
| AU | 729454 | 2/2001 |
| AU | 743316 | 1/2002 |
| AU | 200195225 A1 | 1/2002 |
| CA | 2012312 C | 9/1990 |
| CA | 2370628 A1 | 10/2000 |
| DE | 199 03 713.2 | 1/1999 |
| DE | 101 00586 | 4/2002 |
| EP | 0 213 921 A2 | 3/1987 |
| EP | 0 281 380 A2 | 9/1988 |
| EP | 0 286 224 A2 | 10/1988 |
| EP | 0 300 680 A2 | 1/1989 |
| EP | 0 303 516 A2 | 2/1989 |
| EP | 0 306 347 A2 | 3/1989 |
| EP | 0 308 066 A2 | 3/1989 |
| EP | 0 318 281 A2 | 5/1989 |
| EP | 0 325 018 A2 | 7/1989 |
| EP | 0 347 501 A1 | 12/1989 |
| EP | 0 350 151 A2 | 1/1990 |
| EP | 0 213 921 B1 | 8/1990 |
| EP | 0 306 347 A3 | 10/1990 |
| EP | 0 318 281 A3 | 10/1990 |
| EP | 0 350 151 A3 | 10/1990 |
| EP | 0 308 066 A3 | 1/1991 |
| EP | 0 300 680 A3 | 6/1991 |
| EP | 0 242 0161 B1 | 1/1992 |
| EP | 0 286 224 B1 | 11/1992 |
| EP | 0 560 156 A2 | 9/1993 |
| EP | 0 350 151 B1 | 3/1994 |
| EP | 0 303 516 B1 | 7/1994 |
| EP | 0 306 347 B1 | 5/1995 |
| EP | 0 465 572 B1 | 6/1995 |
| EP | 0 281 380 B1 | 11/1995 |
| EP | 0 308 066 B1 | 12/1995 |
| EP | 0 300 680 B1 | 9/1996 |
| EP | 0 242 016 A1 | 10/1997 |
| EP | 0 921 195 A1 | 6/1999 |
| EP | 0 983 370 A1 | 3/2000 |
| EP | 1 229 134 A2 | 8/2002 |
| EP | 0 983 370 B1 | 9/2003 |
| EP | 1 229 134 A3 | 1/2004 |
| GB | 2353282 A | 2/2001 |
| GB | 2377221 A | 1/2003 |
| JP | 09-110894 A | 4/1997 |
| JP | 09-227413 A | 9/1997 |
| WO | WO 90/11682 A1 | 10/1990 |
| WO | WO 90/12094 A1 | 10/1990 |
| WO | WO 90/12488 A2 | 11/1990 |
| WO | WO 90/14090 A1 | 11/1990 |
| WO | WO 92/18522 A1 | 10/1992 |
| WO | WO 92/19732 A1 | 11/1992 |
| WO | WO 93/17098 A1 | 9/1993 |
| WO | WO 93/23551 A1 | 11/1993 |
| WO | WO 94/01550 A1 | 1/1994 |
| WO | WO 94/17194 A1 | 8/1994 |
| WO | WO 95/03406 A2 | 2/1995 |
| WO | WO 95/10607 A1 | 4/1995 |
| WO | WO 95/15378 | 6/1995 |
| WO | WO 95/18223 A1 | 7/1995 |
| WO | WO 95/18854 A1 | 7/1995 |
| WO | WO 95/23225 A2 | 8/1995 |
| WO | WO 95/03406 A3 | 9/1995 |
| WO | WO 95/27783 A1 | 10/1995 |
| WO | WO 95/34668 A2 | 12/1995 |
| WO | WO 95/34668 A3 | 12/1995 |
| WO | WO 96/08558 A1 | 3/1996 |
| WO | WO 96/20951 | 7/1996 |
| WO | WO 95/35706 A1 | 11/1996 |
| WO | WO 97/01952 A1 | 1/1997 |
| WO | WO 97/07668 A1 | 3/1997 |
| WO | WO 97/10360 A1 | 3/1997 |
| WO | WO 97/11170 | 3/1997 |
| WO | WO 97/34638 A1 | 9/1997 |
| WO | WO 97/35965 | 10/1997 |
| WO | WO 97/44450 A1 | 11/1997 |
| WO | WO 97/48793 | 12/1997 |
| WO | WO 98/05770 A3 | 3/1998 |
| WO | WO 98/18811 A1 | 5/1998 |
| WO | WO 98/36083 | 8/1998 |
| WO | WO 98/37213 A1 | 8/1998 |
| WO | WO 98/44138 A1 | 10/1998 |
| WO | WO 98/53083 A1 | 11/1998 |
| WO | WO 99/09045 A1 | 2/1999 |
| WO | WO 99/15682 A2 | 4/1999 |
| WO | WO 99/25853 A1 | 5/1999 |
| WO | WO 99/32619 | 7/1999 |
| WO | WO 99/38537 | 8/1999 |
| WO | WO 99/49029 | 9/1999 |
| WO | WO 99/53050 | 10/1999 |
| WO | WO 99/61631 | 12/1999 |
| WO | WO 99/61636 | 12/1999 |
| WO | WO 00/01846 | 1/2000 |
| WO | WO 00/44895 | 8/2000 |
| WO | WO 00/44914 | 8/2000 |
| WO | WO 00/49035 | 8/2000 |

| | | |
|---|---|---|
| WO | WO 00/63364 | 10/2000 |
| WO | WO 01/04313 A1 | 1/2001 |
| WO | WO 01/29058 | 4/2001 |
| WO | WO 01/36646 | 5/2001 |
| WO | WO 01/48183 A2 | 7/2001 |
| WO | WO 01/68836 | 9/2001 |
| WO | WO 01/70949 A1 | 9/2001 |
| WO | WO 01/75164 | 10/2001 |
| WO | WO 01/88114 A2 | 11/2001 |
| WO | WO 01/88121 | 11/2001 |
| WO | WO 01/48183 A3 | 12/2001 |
| WO | WO 01/88114 A3 | 6/2002 |
| WO | WO 02/044321 A2 | 6/2002 |
| WO | WO 03/006477 A1 | 1/2003 |
| WO | WO 03/022052 A1 | 3/2003 |
| WO | WO 03/027298 A1 | 4/2003 |
| WO | WO 03/056012 A1 | 7/2003 |
| WO | WO 02/044321 A3 | 10/2003 |

OTHER PUBLICATIONS

U.S. Appl. No. 60/117,635, Not Published, Li et al.
U.S. Appl. No. 60/130,377, Not Published, Pachuk et al.
"Somatic cell," on-line medical dictionary, http://cancerweb.ncl.ac.uk/cgi-bin/ (Jan. 2006).
Agrawal et at, "RNA Interference: Biology, Mechanism, and Applications" *Microb. Mol. Biol Rev.* 67:657-685 (2003).
Agrawal et al., "Self-Stabilized Oligonucleotides as Novel Antisense Agents," in *Delivery Strategies: antisense oligonucleotide therapeutics*, Ahktar et al., Eds., pp. 105-121 CRC Press, Inc., Boca Raton, Florida (1995).
Agrawal, "Antisense oligonucleotides: towards clinical trials," *TIBTECH* 14: 376-387 (1996).
Akgun at al., "Palindrome Resolution and Recombination in the Mammalian Germ Line", *Mol. Cell. Biol.* 17: 5559-5570 (Sep. 1997).
Akhtar et al., "Anti-HIV therapy with antisense oligonucleotides and ribozymes: realistic approaches or expensive myths?" *J. Antimicrob. Chemother*. 38: 159-165 (1996).
Ambion, "pT7/T3 18" and "pT7/T3 19" 4 pages (date unknown).
Anderson, "Human gene therapy," *Nature* 392:25-30 (1998).
Annex A filed in EP 99 910 039.9.
Annex B filed in EP 99 910 039.9 (Sep. 9, 2005).
Annex C filed in EP 99 910 039.9 (Sep. 9, 2005).
Annex D filed in EP 99 910 039.9 (Sep. 9, 2005).
Appeal against decision to refuse a European patent application issued Jul. 11, 2005. filed in EP 99 910 039.9 (Sep. 9, 2005).
Assaad et al., "Epigenetic repeat-induced gene silencing (RIGS) in *Arabidopsis*," *Plant Molecular Biology* 22(6): 1067-1085(1993).
Author unknown, "Breakthrough of the Year #4: Still hot," *Science* 302:2038-2045 (2003).
Balmer et al., "Transduction of Human CD34+ Hematopoietic Progenitor Cells by a Retroviral Vector Expressing an RRE Decoy Inhibits Human Immunodeficiency Virus Type1 Replication in Myelomonocytic Cells Produced in Long-Term Culture," *J. Virol.* 70:4352-4360 (1996).
Balandin et al., "Silencing of a β-1-3-glucanase transgene is overcome during seed formation," *Plant Molecular Biology* 34(1):125-137 (1997).
Barbeau et al., "Characterization of the human and mouse Fli-1 promoter regions," *Biochim. Biophys. Acta* 1307: 220-232 (1996).
Barlow et al., "Interferon synthesis in the early post-implantation mouse embryo," *Differentiation* 27:229-235 (1984).
Bass, "RNA interference: The short answer," *Nature* 411:428-429 (2001).
Baulcombe, "RNA as a target and an initiator of post-transcriptional gene silencing in transgenic plants," *Plant Molecular Biology* 32(1-2):79-88 (1996).
Baum et al.,"Inhibition of Protein Synthesis in Reticulocyle Lysates by a Double-Stranded RNA Component in Hela mRNA," *Biochem. Biophys. Res. Commun* 114:41-49 (1983).
Beretta et al, "Expression of the protein kinase PKR is modulated by IRF-1 and is reduced in 5q- associated leukemias," *Oncogene* 12:1593-1596 (1996).

Betz, "RNAi: RNA Interference," Promega Notes Magazine, No. 83, pp. 33-36 (2003).
Bevec et al., "Constitutive Expression of Chimeric *Neo*-Rev Response Element Transcripts Suppresses HIV-1 Replication in Human CD4+T Lymphocytes," *Hum. Gene Ther.* 5:193-201 (1994).
Bevilacqua, et al., "Antisense RNA inhibits endogenous gene expression in mouse preimplantation embryos: Lack of double-stranded RNA "melting" activity," *Proc. Natl. Acad. Sci. USA* 85:831-835 (1988).
Bhan et al., "2',S'-Linked Oligo-3'-deoxyribonucleoside hosphorothiate chimeras: thermal stability and antisense inhibition of gene expression" *Nucl. Acids Res.* 1(16):3310-3317 (1997).
Bigler et al., "Novel location and function of a thyroid hormone response element," *Embo J.* 14:5710-5723 (1995).
Billy et al. "Specific interference with gene expression induced by long, double stranded RNA in mouse embryonal teratocarcinoma cell lines," *Proc. Natl. Acad. Sci. USA* 98(25):14428-14433 (2001).
Bingham, "Cosuppression Comes to the Animals," *Cell* 90(3):385-387 (1997).
Birchler et al., "Making noise about silence: repression of repeated genes in animals" *Curr. Opin. Genet. Develop*. 10:211-216 (2000).
Bisat et al., "Differential and cell type specific expression of murine alpha-interferon genes is regulated on the transcriptional level," *Nucl. Acids Res.* 13:6067-6083 (1988).
Boldin et al., "Involvement of MACH, a Novel MORT1/FADD-Interacting Protease, in Fas/APO-1- and TNF Receptor-induced Cell Death" *Cell* 85:803-815 (1996).
Borecky et al., "Therapeutic Use of Double-Stranded RNAs in Man" *Tex. Rep. Biol. Med.* 14:575.581 (1981-1982).
Braich et al., "Regiospecific Solid-Phase Synthesis of Branched Oligonueleotideri. Effect of Vicinal 2',5'-(or 2',3'-) and 3',5' Phosphodiester Linkages on the Formation of Hairpin DNA" *Bioconjugate Chem.* 8:370-377 (1997).
Brand et al., "The Tat Protein Of Human Immunodeficieny Virus Type 1 Is a Substrate and Inhibitor of the Interferon-induced, Virally Activated Protein Kinase, PKR," *J. Biol. Chem.* 272:8388-8395 (1997).
Brigneti er al., "Viral pathogenicity determinants are suppressors of transgene silencing in *Nicotiana benthamiana*," *Embo J.* 17(22):6739-6746 (1998).
Brown et al., "Identification through Overexpression and Tagging of the Variant Type of the Mouse H1 e and Hi c Genes," *J. Biol. Chem.* 268:713-718 (1993).
Brummelkamp et al., "Stable suppression of tumorigenicity by virus-mediated RNA," *Cancer Cell* 2:243-247 (2002).
Brummelkamp et al., "A System for Stable Expression of Short Interfering RNAs in Mammalian Cells," *Science* 296:550-553 (2002).
Brummell et al., "Inverted repeat of a heterologous 3'-untranslated region for high-efficiency, high-throughput gene silencing" *Plant J.* 33:793-800 (2003).
Buchan et al., "Characterization of three non-peptide endothelin receptor ligands using human cloned $ET_a$ and $ET_b$ receptors," *Br. J. Pharrnacol.* 122: 1251-1257 (1994).
Burke at al., "Appearance of Interferon Induciblility and Sensitivity During Differentiation of Murine Tetrocarcinoma Cells in Vitro," *Cell* 13(2):243-248 (1978).
Cameron et al., "Specific gene suppression by. engineered ribozymes in monkey cells," *Proc. Natl. Acad Sci*., USA 1989, .86:9139-9143.
Cameron et al., "Multiple Domains in a Ribozyme Construct Confer Increased Suppressive Activity in Monkey. Cells" *Antisense Res. Develop.* 4:87.94 (1994).
Cameron et al., "Inhibition of gene expression by a short sense fragment," *Nucl. Acids Res.* 19(3):469-475 (1991).
Chernajovsky et al., "Human Kinesin Light (β) Chain Gene: DNA Sequence and Functional Characterization of Its Promoter and First Exon," *DNA Cell Biol.* 15: 965-974 (1996).
Christy et al., "Functional Analysis of the Long Terminal Repeats of Intracisternal A-Particle Genes: Sequences within the U3 Region Determine Both the Efficiency and Direction of Promoter Activity," *Mol. Cell. Biol.* 8:1093-1102 (1988).

Chuah et al., "Inhibition of Human Immunodeficiency Virus Type-1 by Retroviral Vectors Expressing Antisense-TAR," *Human Gene Therapy* 5:1467-1475 (1994).

Clusel et al., "Ex vivo regulation of specific gene expression by nanomolar concentration of double-stranded dumbbell oligonucleotides," *Nucl. Acids Res.* 21:3405-3411 (1993).

Clusel et al., "Inhibition of HSV-1 Proliferation by Decoy Phosphodiester Oligonucleotides Containing ICP4 Recognition Sequences," *Gene Expression* 4:301-309 (1995).

Cogoni et al., "Suppression of gene expression by homologous transgenes," *Antonie Van Leeuwenhoek* 65(3):205-209 (1994).

Cogoni et al., "Transgene silencing of the al-1 gene in vegetative cells of Neurospora is mediated by a cytoplasmic effector and does not depend on DNA-DNA interactions or DNA methylation," *Embo J.* 15(12):3153-3163 (1996).

Cogoni et al., "Isolation of quelling-defective (qde) mutants impaired in posttranscriptional transgene-induced gene silencing in *Neurospora crassa*," Proc. Natl. QAcad. Sci. USA 94(19):10233-10238 (1997).

Cogoni et al., "Post-transcriptional gene silencing across kingdoms" *Curr. Opin. Genet. Devel.* 10:638-643 (2000).

Cogoni et al., "Gene silencing in *Neurospora crassa* requires a protein homologous to RNA-dependent RNA polymerase," *Nature* 399:166-160 (1999).

Cogoni et al., "Posttranscriptional Gene Silencing in *Neurospora* by a RecQ DNA Helicase," *Science* 286:2342-2344 (1999).

Cohli et al., "Inhibition of HIV-1 Multiplication in a Human CD4+Lymphocytic Cell Line Expressing Antisense and Sense RNA Molecules Containing HIV-1 Packaging Signal and Rev Response Element(s)," *Antisense Research and Development* 4:19-26 (1994).

Coleman et al., "The Use of RNAs Complementary to Specific mRNAs to Regulate the Expression of Individual Bacterial Genes" *Cell* 37:429-436 (1984).

The European Register for DE 199 03 713.2.

The European Register for WO 00/63364.

The European Register for WO 00/44914.

Courtney-Gutterson et al., "Modification of Flower Color in Florist's Chrysanthemum: Production of White-Flowering Variety Through Molecular Genetics," *Biotechnology* 12(3):268-271 (1994).

Couzin, "Small RNAs Make Big Splash" *Science* 298:2296-2297 (2002).

Czauderna et al., "Structural variations and stabilising modifications of synthetic siRNAs in mammalian cells" *Nucl. Acids Res.* 31(11):1-12 (2003).

Dalmay et al., "An RNA-Dependent RNA Polymerase Gene in *Arabidopsis* Is Required for Posttranscriptional Gene Silencing Mediated by a Transgene but Not by a Virus," *Cell* 101:543-553 (2000).

de Carvalho et al., "Suppression of β-1,3-glucanase transgene expression in homozygous Plants," *Embo J.* 11(7):2595-2602 (1992).

de Carvalho Niebel et al., "Post-Transcriptional Cosuppression of β-1,3-Glucanase Genes Does Not Affect Acculmulation of Transgene Nuclear mRNA," *Plant Cell* 7(3):347-358 (1995).

De Lange et al., "Suppression of Flavonoid Flower Pigmentation Genes in *Petunia hybrida* by the Introduction of Antisense and Sense Genes," *Current Topics in Microbiology and Immunology* 197:57-75 (1995).

Decision to refuse a European patent application dated Jul. 11, 2005, filed in EP 99 910 039.9, 13 pages.

Decoy et al., "Anti sense DNA Down-regulates Protein Kinase C-e and Enhances Vasopressin-stimulated Na+Absorption In Rabbit Cortical Collecting Duct," *J. Clin. Invest.* 95:2749-2756 (1995).

Dopicker et al., "Post-transcriptional gene silencing in plants," *Current Opinion in Cell Biology* 9(3):373-382 (1997).

Di Serio et al., "Sense- and antisense-mediated gene silencing in tobacco is inhibited by the same viral suppressors and is associated with accumulation of small RNAs." *Proc. Natl. Acad. Sci. USA* 98:6506-6510 (2001).

Ding, "RNA silencing," *Current Opinion in Biotechnology* 11:152-156 (2000).

Dobrikova et al., "T7 DNA-dependent RNA polymerase can transcribe RNA from tick-borne encephalitis virus (TBEV) cDNA with SP6 promoter," *FEBS Lett.* 382:327-329 (1996).

Doench et al., "siRNAs can function as miRNAs" *Genes. Dev.* 17:438-442 (2003).

Dolnick. "Naturally Occurring Antisense RNA," Pharm. Ther. 75:1-79-184 (1997).

Domeier et al., "A Link Between RNA Interference and Nonsense-Mediated Decay in *Caenorhabditis elegans*," *Science* 289:1928-1930 (2000).

Dorer et al., "Expansions of Transgene Repeats Cause Heterochromatin Formation and Gene Silencing in Drosophilia," *Cell* 77:993-1002 (1994).

Dorer er al., "Transgene Repeat Arrays Interact with Distant Heterochromarin and Cause Silencing in *cis* and *trans*," *Genetics.* 147(3):1181-1190 (1997).

Dougherty et al, "RNA-Mediated Virus Resistance In Transgenic Plants: Exploitation Of A Cellular Pathway Possibly Involved In RNA Degradation," *Mol. Plant Microbe Interactions* 7(5):544-552 (1994).

Dronkert et al., "Mouse *RAD54* Affects DNA Double-Strand Break Repair and Sister Chromatid Exchange," *Mol. Cell. Biol.* 20:3147-3156 (2000).

Dykxthoorn et al.; "Killing the Messenger: Short RNAs that Silence Gene Expression" *Nature Reviews Molecular Cell Biology* 4:457-467 (2003).

Elbashir et al., "Functional Anatomy of siRNAs for mediating efficient RNAi in *Drosophila melanogaster* embryo lysate" *Embo J.* 20(23):6877-6888 (2001).

Ekenberg et al., "RNse Protection Assay System: A Versatile Technique for the Analysis of RNA," Promega Notes Magazine, 1994, 46:14, pp. 14-17.

Elbashir et al., "Analysis of gene function in somatic mammalian cells using small interfering RNAs," *Methods* 26:199-213 (2002).

Elroy-Stein et al., "Cytoplasmic expression system based on constitutive synthesis of bacteriophage T7 RNA polymerase in mammalian cells," *Proc. Natl. Acad. Sci. USA* 87:6743-6747 (1990).

Engdahl et al., "A two unit antisense RNA cassette test system for silencing of target genes," *Nucl. Acids Res.* 25(16):3218-3227 (1997).

English et al., "Suppression of Virus Accumulation in Transgenic Plants Exhibiting Silencing of Nuclear Genes," *Plant Cell* 8(2):179-188 (1996).

Escude et al., "Stable triple helices formed by oligonucleotide N3' → P5' phosphoramidates inhibit transcription elongation," *Proc. Natl. Acad. Sci. USA* 93:4365-4369 (Apr. 1996).

European Search Report mailed Jun. 3, 2005, for European patent application No. 04015041.9, filed Mar. 19, 1999, 4 pages.

Extract from Henderson's Dictionary of Biological Terms, 10th Edition, "blastomere," (1989).

Extract from Henderson's Dictionary of Biological Terms, 10th Edition, "somatic cells," (1989).

Extract from the New Oxford Dictionary of English, "somatic cells," (1998).

Extract from Henderson's Dictionary of Biological Terms, 10th Edition, "totipotent," (1989).

Faruqi et al., "IFN-γ Inhibits Double-Stranderd RNA-Induced E-Selectin Expression in Human Endothelial Cells," *J. Immunol.* 159:3989-3994 (1997).

Fiaschi et al., "The 5'-untranslated region of the human muscle acylphosphatase mRNA has an inhibitory effect on protein expression," *FEBS Lett.* 417:130-134 (1997).

Finkler et al., "Immunity and resistance to the KP6 toxin of *Ustilago maydis*," *Mol. Gen. Genet.* 233:395-403 (1992).

Francis et al., "Control of β-Interferon Expression in Murine Embryonal Carcinoma F9 Cells," *Mol. Cell. Biol.* 9:3553-3556 (1989).

Fraser et al., "Effects of c-*myc* first exons and 5' synthetic hairpins on RNA translation in oocytes and early embryos of *Xenopus laevis*," *Oncogene* 12(6):1223-1230 (1996).

Fuerst et al., "Eukaryotic transient-expression system based on recombinant vaccinia virus that synthesizes bacteriophage T7 RNA polymerase," *Proc. Natl. Acad. Sci. USA* 83:8122-8126 (1986).

Gao et al., "Human genes encoding u3 SnRNA associate with coiled bodies in interphase cells and are clustered on chromosome 17p11.2 in a complex inverted repeat structure," *Nucl. Acids Res.* 25:4740-4747 (1997).

Garrick at al., "Repeat-induced gene silencing in mammals," *Nature Genetics* 18(1):56-59 (1998).

Gervaix et al., "Multigene Antiviral Vectors Inhibit Diverse Human Immunodeficiency Virus Type 1 Clades," *J. Virol.* 71(4):3048-3053 (1997).

Gessani et al., "Activators of Protein Kinase C Enhance Accumulation of interferon-β mRNA in Murine Cell Lines," *J. Interferon Res.* 9:543-550 (1989).

Gimmi el al., "alterations in the pre-mRNA topology of the bovine growth hormone polyadenylation region decrease poly(A) site efficiency," *Nucl. Acids Res.* 17:6983-6998 (1989).

Giordano et al., "RNAi Triggered by Symmetrically Transcribed Transgenes in *Drosophila melanogaster*" *Genetics* 160:637-648 (2000).

Giovannangeli et al., "Accessibility of nuclear DNA to triplex-forming oligonucleotides: the integrated HIV-1 provirus as a target," *Proc. Natl. Acad. Sci. USA* 94:79-84 (1997).

Gitlin et al., "Poliovirus Escape from RNA Interference: Short Interfering RNA-Target Recognition and Implications for Therapeutic Approaches," *J. Virol.* 79:1027-1035 (2005).

Goff et al., "Analysis of Hoxd-13 and Hoxd-11 Misexpression in Chick Limb Buds Reveals that Hox Genes Affect Both Bone Condensation and Growth," *Development* 124:627-636 (1997).

Good et al:, "Expression of small, therapeutic RNAs in human cell nuclei," *Gene Ther*. 4(1): 45-54 (1997).

Grabarek et al., "Efficient Delivery of dsRNA into Zona-enclosed Mouse Oocytes and Preimplantation Embryos by Electroporation," *Genesis* 32(4):269-276 (2002).

Grabarek et al., "RNA Interference by Production of Short Hairpin dsRNA in ES Cells, Their Differentiated Derivatives, and in Somatic Cell Lines," *Biotechniques* 34(4):734-744 (Apr. 2003).

Graham et al., "A Rapid and Reliable Method to Create Tandem Arrays of Short DNA Sequences," *BioTech.* 13;780-789 (1992).

Graham et al., "RNA Transcripts of The Human Immunodeficiency Virus Transactivation Response Element Can Inhibit Action of The Viral Transactivator," *Proc. Natl. Acad. Sci. USA* 87:5817-5821 (1990).

Grasby et al., "Purine Functional Groups in Essential Residues of the Hairpin Ribozyme Required for Catalytic Cleavage of RNA" *Biochemistry* 34:4068-4076 (1995).

Griffey et al, "2'-Aminopropyl Ribonucleotides: A Zwitterrionic Modification That Enhances The Exonuclease Resistance and Biological Activity of Antisense Oligonucleotides" *J. Med. Chem.* 39:5100-5109 (1996).

Groger et al., "Directional Antisense and cDNA Cloning Using Epstein-Barr Virus Episomal Expression Vectors," *Gene* 81:285-294 (1989).

Gryaznov et al., "Template Controlled Coupling and Recombination of Oligonucleotide Blocks Containing Thiophosphoryl Groups" *Nucl. Acids Res.* 21(6):1403-1408 (1993).

Gura, "A silence that speaks volumes." *Nature* 404:804-808 (2000).

Ha et al., "A Bulged 1 in-4/1 in-14 RNA Duplex is Sufficient For *Caenorhabditis elegans* 1 in-14 Temporal Gradient Formation" *Genes Dev*. 10:3041-3050 (1996).

Hacker et al., "Expression of SRY, The Mouse Sex Determining Gene," *Development* 121:1603-1614 (1995).

Haggerty et al., "An embryonic DNA-binding protein specific for a region of the human IFNβ$_1$ promoter," *Nucl. Acids Res.* 16:10575-10592 (1988).

Haines et al., "Cellular Response To Double-Stranded RNA," *J. Cell. Biochem*. 46:9-20 (1991).

Hamilton et al., "A tranageno with repeated DNA causes high frequency, post-transcriptional suppression of ACC-oxidase gene expression in tomato," *Plant J*. 15(6):737-746 (1998).

Hammond et al., "An RNA-directed nuclease mediates post-transcriptional gene silencing in Drosophila cells," *Nature* 404:293.296 (2000).

Hannon, "RNA Interference" *Nature* 418:244-251 (2002).

Harada et al., "Absence of the Type I IFN System in EC Cells: Transcriptional Activator (IRF-1) and Repressor (IRF-2) Genes are Developmentally Regulated," *Cell* 63:303-312 (1990).

Harbinder et al., "Genetically Targeted Cell Disruption In *Caenorhabditis elegans*," *Proc. Natl. Acad. Sci. USA* 94:13128-13133 (1997).

Harborth et al. "Sequence, Chemical, and Structural Variation of Small Interfering RNAs and SHort Hairpin RNAs and the Effect on Mammalian Gene Silencing" *Antisense and Nucleic Acid Drug Development* 13:83-105 (2003).

Harborth et al. "identification of essential genes in cultured mammalian cells using small interfering RNAs," *J. Cell Science* 114:4557-4565 (2001).

Harcourt et al., "Ebola Virus Inhibits Induction of Genes by Double-Stranded RNA in Endothelial Cells," *Virology* 252:179-188 (1998).

Harfe et al., "Analysis of a *Caenorhabditis elegans* Twist Homolog Identifies Conserved and Divergent Aspects of Mesodermal Patterning," *Genes Dev*. 12:2623-2635 (1998).

Henderson et al., "Instability of a Plasmid-Borne Interved Repeat in *Saccharomyces cerevisiae,*" *Genetics* 134:57-62 (1993).

Henry et al., "Mechanism of interferon action. Translational control and the RNA-dependent protein kinase (PKR): antagonists of PKR enhance the translational activity of mRNAs that include a 161 nucleotide region from reovirus S1 rnRNA," *J. Biol. Regulators Homeostat. Agents* 8:15-24 (1994).

Hirashima et al., "Artificial Immune System against Viral Infection Involving Antisense RNA targeted to the 5'-Terminal Noncoding Region of Coliphage SP RNA," *J. Biochem.* 106:163-166 (1989).

Hirashima et al., "Engineering of the mRNA-interfering Complementary RNA Immune System Against Viral Infection," *Proc. Natl. Acad. Sci. USA* 83:7726-7730 (1986).

Hoke et el., "Effects of Phosporothioato Capping On Antisense Oligonucleotide Stability, Hybridization and Antiviral Efficacy Versus Herpes Simplex Virus Infection" *Nucl. Acids Res.* 19(20):5743-5748 (1991).

Holen et al., "Positional effects of short interfering RNAs targeting the human coagulation trigger Tissue Factor" *Nucl. Acids Res.* 30(8):1 757-1766 (2002).

Hungarian Patent Office Search Report mailed Jul. 13, 2004 for Hungarian patent application No. P0101225, 1 page.

Imazeki et al., "Integrated Structures of Duck Hepatitis B Virus DNA in Hepatocellular Carcinoma," *J. Virol* 62:861-865 (1988).

International Search Report mailed on May 10, 1999, for PCT patent application No. PCT/AU99/00195, filed on Mar. 19, 1999: 3 pages.

International Search Report mailed on May 10, 2001, for PCT patent application No. PCT/AU01/00297, filed on Mar. 16. 2001:3 pages.

International Search Report mailed on Nov. 14, 2002, for PCT patent application No. PCT/AU02/01326, filed on Sep. 27, 2002: 5 pages.

Invitrogen, Map for pcDNAI, 1 page (date unknown).

James, "Towards gene-inhibition therapy: a review of progress and prospects in the field of antiviral antisense nucleic acids and ribozymes," *Antiviral Chem. & Chemother*. 2(4):191-214 (1991).

Jorgensen et al., "Do Unintended Antisense Transcripts Contribute To Sense Cosuppression in Plants," *TIG* 15:11-12 (1999).

Jorgensen, "Altered gene expression in plants due to trans interactions between homologous genes," *Trends Biotechnol.* 8(12):340-344 (1990).

Jorgensen et al., "Chalcone synthase cosuppression phenotypes in petunia flowers: comparison of sense vs. antisense constructs and single-copy vs. complex T-DNA sequences," *Plant Mol. Biol.* 31(5):957-973 (1996).

Kappel et al., "Regulating gene expression in transgenic animals," *Curr. Opin. Biotechnol.* 3:548-553 (1992).

Katsuki et al., "Conversion of Normal Behavior to Shiverer by Myelin Basic Protein Antisense cDNA in Transgenic Mice," *Science* 241(4865):593-595 (1988).

Kennerdell et al., "Heritable gene silencing in Drosophila using double-stranded RNa," 2000. *Nature Biotechnology*, 18:896-898.

Kibler et al., "Double-stranded RNA is a Trigger for Apoptosis in Vaccinia Virus-Infected Cells." *J. Virol*. 71:1992-2003 (1997).

Kirchhoff et al., "IRF-1 induced cell growth inhibition and interferon induction requires the activity of the protein kinase PKR," *Oncogene* 11:439-445 (1995).

Kitabwalla et al., "RNA Interference—A New Weapon Against HIV and Beyond" *New Engl. J. Med.* 347(17):1364-1367(2002).

Klaff et al., "RNA Structure and The Regulation of Gene Expression," *Plant Mol. Biol.* 32:89-106 (1996).

Klink et al., "The Efficacy of RNAi in the Study of the Plant Cytoskeleton" *J. Plant Growth Reg.* 19:371-384 (2000).

Knoester et al., "Modulation of stress-inducible ethylene biosynthesis by sense and antisense gene expression in tobacco," *Plant Science* 126:173-183 (1997).

Kook et al., "The effect of antisense inhibition of urokinase receptor in human squamous cell carcinoma on malignancy," *EMBO J.* 13(17):3983-3991 (1994).

Konstantinova et al., "Inhibition of immunodeficiency virus type 1 by RNA interference using long-hairpin RNA," 2006. *Gene Therapy*. pp. 1-11.

Kowolik et al., "Locus Control Region of the Human CD2 Gene in a Lentivirus Vector Confers Position-Independent Transgene Expression" *J. Virol.* 75(10):4641-4648 (2001).

Kowolik et al, "Preferential Transduction of Human Hepatocytes with Lentiviral Vectors Pseudotyped By Sendai Virus F Protein" *Molecular Therapy* 5(6):762-769 (2002).

Kozak, "Influences of mRNA secondary structure on initiation by eukaryotic ribosomes," *Proc. Natl. Acad. Sci. USA* 83:2850-2854 (1986).

Kozak, "Circumstances and Mechanisms of Inhibition of Translation by Secondary Structure in Euearyotic mRNAs,"*Mol. Cell. Biol.* 9:5134-5142 (1989).

Kreutzer, "Specific inhibition of viral gene expression by double-stranded RNA in vitro" Fall Meeting S169.

Krystal et al., "Multiple Mechanisms for Transcriptional Regulation of the myc Gene Family in Small-Cell Lung Cancer," *Mol. Cell. Biol.* 8:3373-3381 (1988).

Krystal et al., "N-*myc* mRNA Forms an RNA-RNA Duplex with Endogenous Antisense Transcripts," *Mol. Cell. Biol.* 10:4180-4191 (1990).

Kunz et al., "Developmentally regulated silencing and reactivaation of tobacco chitinase transgene expression," *Plant J.* 10(3):437-450 (1996).

Kurreck, "Antisense technologies. Improvement thorough novel chemical modifications," *Eur. J. Biochem* 270:1628-1644 (2003).

Leach et al., "Viability of λ phages carrying a perfect palindrome in the absence of recombination nucleases," *Nature* 305:448-451 (1983).

Leach et al., Long DNA palindromes, cruciform structures. genetic instability and secondary structure repair, *BioEssays* 16:893-900 (1994).

Lee et al., "The *C. elegans* Heterochronic Gene *lin*-4 Encodes Small RNAs with Antisense Complementarity to *lin-14*," *Cell* 75:843-854 (1993).

Lee et al, "The Hemagglutinin Genes *hagB* and *hagC* of *Porphyromonas gingivalis* Are Transcribed in Vivo as Shown by Use of a New Expression Vector," *Infect. Immun.* 64:4802-4810 (1996).

Lee et al., "Inhibition of Human Immunodeficiency Virus Type 1 in Human T Cells by a Potent Rev Response Element Decoy Consisting of 13-Nucleotide Minimal Rev-Binding Domain," *J. Virol.* 68(12):8254-8264 (1994).

Lee et al., "Post-transcriptional gene silencing of ACC synthase in tomato results from cytoplasmic RNA degradation," *Plant J.* 12(5):1127- 1137 (1997).

Lin et al., "Policing Rogue Genes" *Nature* 402:128-129 (1999).

Lindbo et al., "Pathogen-Derived Resistance to a Potyvirus: Immune And Resistant Phenotypes In Transgenic Tobacco Expressing Altered Forms Of A Potyvirus Coat Protein Nucleotide Sequence," *Mol. Plant-Microbe Interactions* 5(2):144-I53 (1992).

Lingelbach et al., "An extended RNA/RNA duplex structure within the coding region of mRNA does not block translational elongation," *Nucl. Acids Res*. 16:3405-3414 (1988).

Lipinski et al., "Experimental and computational approaches to estimate solubility and permeability in drug discovery and development settings" *Advanced Drug Delivery Reviews* 23:3-25 (1997).

Lisziewicz et al.,"Tat-Regulated Production cif Multimerized TAR RNA Inhibits HIV-1 Gene Expression" *New Biologist* 3:82-89 (1991).

Lisziewicz et al., "Inhibition of human immunodeficiency virus type 1 replication by regulated expression of a polymeric Tat activation response RNA decoy as a strategy for gene therapy in AlDS," *Proc. Natl. Acad. Sci. USA* 90;8000-8004 (1993).

Lloyd et al., "Identification and Genetic Analysis of *sbcC* mutations in commonly used *recBC sbcB* strains of *Escherichia coli* K-12," *J. Bacteriol*, 164:836-844 (1985).

Longman et al., "Functional characterization of SR and SR-related genes in *Caenorhabditis elegans*," *EMBO J.* 19:1625-1637 (2000).

Loomis et al., "Antisense Rna Inhibition of Expression of a Pair of Tandemly Repeated Genes Results in a Delay in Cell-Cell Adhesion in *Dictyostelium*," *Antisense Res. Dev.* 1:255-260 (1991).

Ma et al., "Design and Synthesis of RNA Miniduplexes via a Synthetic Linker Approach" *Biochemistry* 32:1751-1758 (1993).

Mace et al., "Interferon-regulated viral replication in chronically HIV1-infected promonocytic U937 cells," *Res. Viral.* 142:213-220 (1991).

Majumdar et al., "Targeted Gene Knockout Mediated by Triple Helix Forming Oligonucleotides" *Nat. Genet.* 20:212-Z14 (1998).

Manche et al., "Interactions Between Double Stranded RNA Regulators and the Protein Kinase DAI" *Mol. Cell. Biol.* 12(11):5238-5248 (1992).

Maratha et aL, "RNA virues as inducers, suppressors and targets of post-transcriptional gene silencing," *Plant Molecular Biology* 43:295-306 (2000).

Marcus et al., "The pGEM$^{db}$-T and pGEM$^{40}$ -$^{T\ Easy\ Vector\ Systems}$," *Promega Notes Magazine*, No. 58, 36-38 (1996).

Marx, "Interfering With Gene Expression," *Science* 288:1370-1372 (2000).

Matthieu et al., "Myelin-Deficient Mutant Mice: An in Vivo Model for Inhibition of Gene Expression by Natural Antisense RNA," *Ann. N. Y. Acad. Sci.* 660:188-192 (1992).

Matzke et al., "How and Why Do Plants Inactivate Homologous (Trans)genes" *Plant Physiol*. 107:679-685 (1995).

Matzke et al., "RNAi Extends Its Reach" *Science* 301:1060-1061 (2003).

Mayne et al., "SV40-transformed normal and DNA-repair-deficient human fibroblasts can be transfected with high frequency but retain only limited amounts of integrated DNA," *Gene* 66:65 (1988).

McCormack et al., "Mechanism of Interferon Action: Identification of a RNA Binding Domain within the N-terminal Region of the Human RNA-Dependent P1/eIF-2α Protein Kinase," *Virology* 188:47-56 (1992).

McKenzie et al., "Xenotransplantation," Eds. Ginns et al., in *Transplantation*, Science Inc., pp. 827-874 (1999).

McManus et al., "Gene Silencing in Mammals By Small Interfering RNAs" *Nat. Rev. Genet*. 3(10):737-747 (2002).

McManus et al., "Gene Silencing using micro-RNA designed hairpins" *RNA* 8:842.850 (2002).

McManus et al., "Small Interfering RNA-Mediated Gene Silencing in T Lymphocytes," *J. Immunol.* 169:5754-5760 (2002).

McNair et al., "Hepatitis delta virus replication in vitro is not affected by interferon-α or —γ despite intact cellular responses to the interferon and dsRNA, " *Gen. Virol.* 75:1371-1378 (1994).

Mercola et al., "Antisense Approaches to Cancer Gene Therapy," *Cancer Gene Ther*. 2:47-59 (1995).

Mette et al., "Transcriptional Silencing And Promoter Methylation Triggered By Double-Stranded RNA," *EMBO J.* 19:5194-5201 (2000).

Meyer, "Repeat-Induced Gene Silencing: Common Mechanisms in Plants and Fungi," *Biol. Chem. Hoppe-Seyler* 377(2)87-95 (1996).

Mikoshiba et al., "Chimeric and Molecular Genetic Analysis of Myelin-Deficient (Shiverer and Mld) Mutant Mice," *Ann. N. Y. Acad. Sci*. 605:166-182 (1990).

Mikoshiba et al., "Molecular biology of myelin basic protein: gene rearrangement and expression of anti-sense RNA in myelin-deficient mutants" *Comp. Biochem. Physiol*. 98:51-61 (1991).

Milhaud et al., "Free and Liposome-Encapsulated Double-Stranded RNAs as Inducers of Interferon, Interleukin-6, and Cellular Toxicity" *J. Interferon Res*. 11:261-265 (1991).

Minutes of Oral Proceeding dated Jul. 12, 2005, filed in EP 99 910 039.9.

Morishita et al., "Role of Transcriptional *cis*-Elements, Angiotensinogen Gene-Activating Elements, of Angiotensinogen Gene in Blood Pressure Regulation," *Hypertension* 27:502-507 (1996).

Moroni et al., "EGF-R Antisense RNA Blocks Expression of the Epidermal Growth Factor Receptor and Suppresses the Transforming Phenotype of a Human Carcinoma Cell Line," *J. Biol. Chem.* 267(4):2714-2722 (1992).

Morris et al., "Small Interfering RNA-Induced Transcriptional Gene Silencing in Human Cells," *Science* 305:1289-1292 (2004).

Moss et al., "The Cold Shock Domain Protein LIN-28 Controls Development Timing in *C. elegans* and is Regulated by the lin-4 RNA" *Cell* 88:637-646 (1997).

Mueller et al,"Homology-dependent resistance: transgenic virus resistance in plants related to homology-dependent gene silencing," *Plant J.* 7(6):1001-1013 (1995).

Muskens et al., "Role of inverted DNA repeats in transcriptional and post-transcriptional gene silencing," *Plant Mol. Biol.* 43:243-260 (2000).

Nagy et al., "Glyceraldehyde-3-phosphate Dehydrogenase Selectively Binds AU-rich RNA in the $NAD^+$-binding Region (Rossmann Fold)," *J. Biol. Chem.* 270:2755-2763 (1995).

Napoli et al., "Introduction of a Chimeric Chalcone Synthase Gene into Petunia Results in Reversible So-Suppression of Homologous Genes in *trans*," *Plant Cell* 2(4):279-289 (1990).

Nellen, et al., "What makes an tnRNA anti-sensa-itive?" *Trends in Biochemical Sciences* 18(11):419-423 (1993).

Nielsen et al., "A novel class of conformationally restricted oligonucleotide analogues: synthesis of 2', 3'-bridged monomers and RNA-selective hybridisation" *Chem. Commun.* 9:825-826 (1997).

Nieth et al., "Modulation of the classical multidrug resistance (MDR) phenotype by RNA interference (RNAi)," *FEBS Letters* 545:144-150 (2003).

Nikiforov et al., "Oligodeoxynucleotides containing 4-thiothymidine and 6-thiodeoxyguanosine as affinity labels for the Eco RV restriction endonuclease and modification methylase, "*Nucl. Acids Res.* 20(6):1209-1214 (1992).

Noguchi et al., "Characterization of an Antisense INr Element in the eIF-2α Gene." *J. Biol. Chem.* 269:29161-29167 (1994).

Okano et al., "Myelin Basic Protein Gene and the Function of Antisense RNA in its Repression in Myelin-Deficient Mutant Mouse," J. *Neurochem.* 56:560-567 (1991).

Paddison et al., "Short hairpin RNAs (shRNAs) induce sequence-specific silencing in mammalian cells" *Genes and Development* 16:948-958 (2002).

Paddison et al., "RNA interference: the new somatic cell genetics?" *Cancer Cell* 2:17-23 (2002).

Pal-Bhadra et al., "Cosuppression in Drosophila: Gene Silencing of Alcohol dehydrogenase by white-Adh Transgenes is Polycomb Dependent," *Cell* 90(3):479-490 (1997).

Palaugui et al., "Transgenes are dispensable for the RNA degradation step of cosuppression," *Plant Biology*.95:9675-9680 (1998).

Palmiter et al., "Transmission Distortion and Mosaicism in an Unusual Transgenic Mouse Pedigree," *Cell* 36:869-877 (1984).

Pang et al., "Nontarget DNA sequences reduce the transgene length necessary for RNA-mediated tospovirus resistance in transgenic plants," *Proc. Natl. Acad. Sci. USA* 94(15):8261-8266 (1997).

Park et al., "Specific inhibition of HIV-1 gene expression by double-stranded RNA." *Nucl. Acids Res.* Suppl. No. 1:219-220 (2001).

Park et al., "Prevention of HIV-1 infection in human peripheral blood mononuclear cells by specific RNA interference," *Nucl. Acids Res.* 30(22):4830-4835 (2002).

Park et al., "Gene silencing mediated by promotor homology occurs at the level of transcription and results in meiotically heritable alterations in methylation and gene activity," *Plant J.* 9(2):183-194 (1996).

Pe'ery et al., "Synthesis and Purification of Single Stranded RNA for Use in Experiments with PKR and in Cell-Free Translation Systems,"*Methods* 11:371-381 (1997).

Pegram et al., "Phase II study of Receptor-Enhanced Chemosensitivity Using Recombinant Humanized Anti-p185$^{HER2neu}$ Monoclonal Antibody Plus Cisplatin in Patients With HER2/Neu-Overexpressing Metastatic Breast Cancer Refractory to Chemotherapy Treatment " *Journal of Clinical Oncology* 16(8):2659-2671 (1998).

Pelletier et al., "Insertion mutagenesis to increase secondary structure within the 5' noncoding region of a eukaryotic mRNA reduces translational efficiency," *Cell* 40:515-526 (1985).

Peng et al., "Development of an MFG-Based Retroviral Vector System for Secretion of High Levels of Functionally Active Human BMP4" *Molecular Therapy* 4(2):95-104 (2001).

Peyman et al., "Molecular Biology, and The Vascular Surgeon," in *Basic Science of Vascular Disease*, Chapter 2, pp. 17-68 (1997).

Piccin et al., "Efficient and Heritable Functional Knock-out of an Adult Phenotype in Drosophila using a GAL4- Driven Hairpin RNA Incorporating a Heterologous Spacer," *Nucl. Acids. Res.* 29(12) E55:1-5 (2001).

Plasterk et al., "The Silence of the Genes," *Curr. Opin. Gen. Dev.* 10:562-567 (2000).

Pratt et al., "Regulation of In Vitro Translation by Double-stranded RNA in Mammalian Cell mRNA Preparations," *Nucl. Acids Res.* 16:3497-3510 (1988).

Putlitz el al.," Specific Inhibition of Hepatitis B Virus Replication By Sense RNA," *Antisense & Nucleic Acid Drug Development* 9:241-252 (1999).

Que et al., "The Frequency and Degree of Cosuppression by Sense Chalcone Synthase Transgenes Are Dependent on Transgene Promoter Strength and Are Reduced by Premature Nonsense Codons in the Transgene Coding Sequence," *Plant Cell* 9:1357-1368 (1997).

Que et al., "Homology-Based Control of Gene Expression Patterns in Transgenic Petunia Flowers," *Developmental Genetics* 22(1):100-109 (1998).

Randall et al., "Clearance of replicating hepatitis C virus replicon RNAs in cell culture by small interfering RNAs," *Proc. Natl. Acad. Sci. USA* 100(1):235-240 (2003).

Raponi et al., "Double-stranded RNA-mediated Gene Silencing in Fission Yeast," *Nucl. Acids Res.* 31:4481-4489 (2003).

Regalado, "Turning Off Genes Sheds New Light on How They Work" *The Wall Street Journal*, 4 pages. (Aug. 2002).

Reply to Summons to attend Oral Proceeding filed May 13, 2005 in European Patent Application No. 99 910 039.9, 9 pages.

Request for correction of minutes filed Aug. 2, 2005 in EP 99 910 039.9, 3 pages.

Resnekov et al., "RNA Secondary Structure Is an Integral Part of the in Vitro Mechanism of Attenuation in Simian Virus 40," *J. Biol. Chem.* 264:9953-9959 (1989).

Reuben et al., "Cloning and Expression of The Rabbit Gastric CCK-A Receptor," *Biochim. Biophys. Acta* 1219:321-327 (1994).

Robertson et al., "Age-dependent silencing of globin transgenes in the mouse," *Nucl. Acids Res.* 24:1465-1471 (1996).

Rodriguez et al., "Regulated Expression of Nuclear Genes by T3 RNA Polymerase and lac Repressor, Using Recombinant Vaccinia Virus Vectors," *J. Virol.* 64:4851-4857 (1990).

Romano of al., "Quelling: transient inactivation of gene expression in Neurospora crassa by transformation with homologous sequences," *Mol. Microbiol.* 6(22):3343-3353 (1992).

Roy et al., "Effect of mRNA secondary structure on the efficiency of Translational Initiation by Eukaryotic Ribosomes," *Eur. J. Biochem.* 191:647-652 (1990).

Ruskin et al., "Mutations in POl1 Increase the Mitotic Instability of Tandem inverted Repeats in *Saccharomyces cerevisiae*," *Genetics* 133:43-56 (1993).

Sabi et al., "Copy Number and Orientation Determine the Susceptibility of a Gene to Silencing by Nearby Heterochromatin in Drosophila," *Genetics* 142:447-458 (1996).

Sadiq et al., "Developmental Regulation of Antisense-Mediated Gene Silencing in Dictyostelium," *Antisense Research & Development* 4(4):263-267 (1994).

Sarver et al., "Ribozymes as Potential Anti-HIV-1 Therapeutics Agents" *Science* 247:1222-1225 (1990).

Schaefer et al., "Antisense RNA control of gene expression in bacteriophage P22. 1. Structures of sar RNA and its target, ant mRNA," *RNA* 3(2):141-156 (1997).

Schaller, "The Role of Sterols in Plant Growth and Development," *Prog. Lipid Res.* 42:163-175 (2003).

Schmidt et al., "Cycloheximide Induction of Aflatoxin Synthesis in a Nontoxigenic Strain of *Aspergillus flavus*" *Bio/Technology* 1:794-795 (1983).

Schmidt, "RNA Interference Detected 20 years ago," *Nat. Biotechnol.* 22:267-268 (2004).

Schmidt et al., "Viral Influences on Aflatoxin Formation by *Aspergillus flavus.*" *Appl. Microbiol. Biotechnol.* 24:248-252 (1966).

Schmitt et al., "Characterization of cloned sequences complementary to F9 cell double-stranded RNA and their expression during differentiation," *Differentiation* 30:205-210 (1986).

Schramke et al., "Hairpin RNAs and Retrotransposon LTRs Effect RNAi and Chromatin-Based Gene Silencing" *Science* 301:1069-1074 (2003).

Schwarz et al., "Evidence that siRNAs Function as Guides, Not Primers in the Drosophila and Human RNAi Pathways," *Molecular Cell* 10:537-548 (2002).

Selker, "Gene Silencing: repeats that count," *Cell* 97 (2):157-160 (1999).

Shaffer, "RNAi Shakes up Bio CEO Investor Conference," *Biotech News* 24:30 (2004).

Sharp, "RNAi and Double-Strand RNA," *Genes Dev.* 13:139-141 (1999).

Shi et al., "A CBP/p300 Homolog Specifies Multiple Differentiation Pathways in *Caenorhabditis elegans*" *Genes Dev.* (12)7:943-955. (1998).

Shinagawa et al., "Generation of Ski-knockdown mice by expressing a long double-strand RNA from an RNA polymerase II promoter." *Genes Dev.* 37:1340-1345 (2003).

Sijen et al., "RNA-Mediated Virus Resistance: Role of Repeated Transgenes and Delineation of Targeted Regions," *Plant Cell* 8(12):2277-2294 (1996).

Silverman, "Role of Sequences Within The First Intron in the Regulation of Expression of Eukaryotic Initiation Factor $2\alpha$," *J. Biol. Chem.* 267:9738-9742 (1992).

Simons, "Naturally Occurring Antisense RNA Control—A Brief Review," *Gene* 72:35-44 (1988).

Singer et al., "Genetic and Epigenetic Inactivation of Repetitive Sequences in *Neurospora crassa*: RIP, DNA Methylation, and Quelling," *Current Topics in Microbiology and Immunology* 197:165-177 (1995).

Sinha, "Large-Scale Synthesis: Approaches to Large-Scale Synthesis of Oligodeoxynecleotides and their Analog" *Antisense From Technology to Therapy Lab Manual and Textbook* 6:30-58 (1997).

Skripkin et al., "Psoralen Crosslinking Between Human Immunodeficiency Virus Type 1 RNA and Primer $tRNA_3^{Lys}$" *Nucl. Acids Res.* 24(3):509-514 (1996).

Smardon et al. "EGO-1 is related to RNA-directed RNA polymerase an functions in germ-line development and RNA interference in *C. elegans,*" *Current Biology* 10(4):169-178 (2000).

Smith et al., "Total Silencing by Intron-spliced Hairpin RNAs." *Nature* 407:319.320 (2000).

Smith et al., "Transgenic plant virus resistance mediated by untranslatable sense RNAs: expression, regulation and fate of nonessential RNAs," *Plant Cell* 6(10):1441-1453 (1994).

Smolinski et al., "Double-Stranded RNA Induces Sickle Erythrocyte Adherence to Endothelium: A Potential Role for Viral Infection in Vaso-Occlusive Pain Episodes in Sickle Cell Anemia." *Blood* 85:2945-2950 (1995).

Smythe et al, "Gene Therapeutic agents: The Use of Ribozymes, Antisene, and RNA Decoys for HIV-1 Infection," *inflamm. Res.* 44:11-15 (1995).

Sonoda et al., "Asymmetric deletion of the junction between the short unique region and the invested repeat does not affect viral growth in culture and vaccine-induced immunity against Marek's disease," *Vaccine* 14:277-284 (1996).

Stam et al., "The Silence of Genes in Transgenic Plants," *Annals of Botany* 79(1):3-12 (1997).

Statement setting out the Grounds of Appeal dated Nov. 11, 2005, filed in EP 99 910 039.9, 11 pages.

Stein et al., "Absence of non-specific effects of RNA interference triggered by long double-stranded RNA in mouse oocytes," *Dev. Biol.* 286(2):464-471 (Sep. 2005).

Steinecke et al., "Expression of a Chimeric Ribozyme Gene Results in Endonueleolytic Cleavage of a Target mRNA and a Concomitant Reduction of Gene Expression in vivo" *Nucl. Acids Res.* 23:1525-1530 (1992).

Stewart et al., "Lentivirus-delivered stable gene silencing by RNAi in primary cells," *RNA* 9:493-501 (2003).

Strauss, "Candidate Gene Silencers Found" *Science* 286: 886 (1999).

Sullenger et al., "Overexpression of TAR Sequences Renders Cells Resistant to Human Immunodeficiency Virus Replication," *Cell* 63:601-608 (1990).

Sullenger et al., "Expression of Chimeric tRNA-Driven Antisense Transcripts Renders NIH 3T3 Cells Highly Resistant to Moloney Murine Leukemia Virus Replication," *Mol. Cell. Biol.* 10:6512-6523 (1990).

Sullenger et al., "Analysis of trans-acting Response Decoy RNA-Mediated Inhibition of Human Immunodeficiency Virus Type 1 Transactivation," *J. Virology* 65(12):6811-6816 (1991).

Sullenger et al., "Tethering Ribozymes to a Retroviral Packaging Signal for Destruction of Viral RNA" *Science.* 262:1566-1569 (1993).

Sun et al., "Ribozyme-mediated Suppression of Moloney Murine Leukemia Virus and Human Immunodeficiency Virus Type I Replication in Permissive Cell Lines," *Proc. Natl. Acad. Sci. USA* 91:9715-9719 (1994).

Sun et al., "Resistance to human immunodeficiency virus type 1 infection conferred by transduction of human peripheral blood lymphocytes with ribozyme, antisense, or polymeric trans-activation response element constructs," *Proc. Natl. Acad. Sci. USA* 92:7272-7276 (1995).

Svoboda et al., "RNAi in Mouse Oocytes and Preimplantation Embryos: Effectiveness of Hairpin dsRNA", Biochem. Biophys. Res. Commun. 287(5):1099-1104 (2001).

Sweetser et al., "Tranegenie mice containing intestinal fatty acid-binding protein-human growth hormone fusion genes exhibit correct regional and cell-specific expression of the reporter gene in their small intestine," *Proc. Natl. Acad. Sci, USA* 85:9611-9615 (1988).

Symington, "Role of RAD52-Epistasis Group Genes In Homologous Recombination and Double-Strand Break Repair," *Microbiol Mol. Biol. Rev.* 66:630-670 (2002).

Table describing sequences used to inhibit viral replication. Annex A filed in EP 99 910 039.9.

Tanaka et al., "Sequence-specific interaction of $\alpha$ $\beta$-anomeric double-stranded DNA with the p50 subunit of NFxB: application to the decoy approach." *Nucl. Acids Res.* 22:3069-3074 (1994).

Tanzer et al., "Characterization of Post-Transcriptionally Suppressed Transgene Expression that Confers Resistance to Tobacco Etch Virus infection in Tobacco," *Plant Cell* 9(8):1411-1423 (1997).

Tavernarakis et al., "Heritable and inducible genetic interference by double-stranded RNA encoded by transgenes," 2000. *Nature Genetics*, 14:180-183.

Thomis, et al., "Mechanism of interferon action: Autoregulation of Rna-dependent P1/eIF-$2\alpha$ protein kinase (PKR) expression in transfected mammalian cells," *Proc. Natl. Acad. Sci. USA* 89:10837-10841 (1992).

Tijsterman et al., "The Genetics of RNA Silencing," *Ann. Rev. Genet.* 36:489-519 (2002).

Tosic et al., "Post-transcriptional events are responsible for low expression of myelin basic protein in myelin deficient mice: role of natural antisense RNA," *EMBO J.* 9:401-406 (1990).

Touchette. "Gene Therapy: Not Ready for Prime Time," *Nat. Med.* 2(1):7-8 (1996).

Uhlmann et al., "Antisense Oligonucleotides: A New Therapeutic Principle" *Chemical Reviews* 9(4):544-584 (1990).

Usdin et al., "SP6 RNA Polymerase containing vaccinia virus for rapid expression of cloned genes in tissue culture," *BioTech.* 14:222-224 (1993).

Vaucheret et al., "A Transcriptionally Active State is Required for Post-Transcriptional Silencing (Cosuppresion) of Nitrate Reductase Host Genes and Transgenes," *Plant Cell* 9(8):1495-1504 (1997).

Van der Krol et al., "Flavonoid Genes in Petunia: Addition of a Limited No. of Gene Copies May Lead to a Suppression of Gene Expression," *Plant Cell* 2(4):291-299 (1990).

Van der Krol et al., "Inhibition of flower pigmentation by antisense CHS genes: promoter and minimal sequence requirements for the antisense effect," *Plant Molecular Biology* 14(4):457-466 (1990).

Van Steeg et al., "The translation in vitro of rat ornithine decarboxylase mRNA is blocked by its 5' untranslated region in a polyamine-independent way," *Biochem. J.* 274:521-526 (1991).

Viville, "Mouse Genetic Manipulation via Homologous Recombination," in *Transgenic Animals*, Houdebine (eds), Harwood academic publishers, France: pp. 307-321 (1997).

Volloch et al., "Evolutionarily conserved elements in the 5' untranslated region of β globin mRNA mediate site-specific priming of a unique hairpin structure during cDNA synthesis," *Nucl. Acids Res.* 22:5302-5309 (1994).

Wall, "Transgenic Livestock: Progress and Prospects for the Future," *Theriogenology* 45:57-68 (1996).

Wang et al., "An Unusual Nucleoporin-Related Messenger Ribonucleic Acid is Present in the Germ Cells of Rat Testis," *Biol. Reprod.* 51:1022-1030 (1994).

Wang et al., "A factor IX-deficient mouse model for hemophilia B gene therapy," *Proc. Natl. Acad. Sci. USA* 94:11563-11566 (1997).

Wargelius et al., "Double-Stranded RNA Induces Specific Developmental Defects in Zebrafish Embryos," *Biochem. Biophys. Res. Commun.* 263:156-161 (1999).

Warren et al., "Comparison of Physical and Genetic Properties of Palindromic DNA Sequences," *J. Bacteriol* 161:1103-1111 (1985).

Wassenegger et at, "Signalling in gene silencing," *Trends Plant Sci.* 4(6):207-209 (1999).

Watson, "A new revision of the sequence of plasmid pBR322," *Gene* 70:399-403 (1988).

Weaver et al., "Introduction by molecular cloning of artifactual inverted sequences at the 5' terminus of the sense strand of bovine parathyroid hormone cDNA" *Proc. Natl. Acad. Sci. USA* 78:4073-4077 (1981).

Wess et al., "Early days for RNAi "*BioCentury* 11(12):A1-23 (2003).

Williams et al., "A mouse locus at which transcription from both DNA strands produces mRNAs complementary at their 3' ends," *Nature* 322:275-279 (1986).

Wolffe, "Repressed repeats express themselves," *Current Biol.* 7:R796 (1997).

Written Opinion mailed on Apr. 17, 2004, for PCT application No. PCT/AU03/01177 filed Sep. 9, 2003: 7 pages.

Wu et al., "Interferon-Stimulated Response Element and NFκB Sites Cooperate to Regulate Double-Stranded RNA-Induced Transcription of the IP-10 Gene," *J. Interferon Res.* 14:357-363 (1994).

Wu et al., "Double-stranded (ds) RNA Binding and Not Dimerization Correlates with the Activation of the dsRNA-dependent Protein Kinase (PKR)," *J. Biol. Chem.* 271:1756-1763 (1996).

Xiong et al., "Signaling properties of mouse and human corticotropin-releasing factor (CRF) receptors: decreased coupling efficiency of human type II CRF receptor," *Endocrin.* 136:1828-1834 (1995).

Yam et al., "Design of HIV Vectors for Efficient Gene Delivery into Human Hematopoietic Cells," *Molecular Therapy* 5(4):479-484 (2002).

Yamamoto et al., "Double-Stranded *nef*RNA Interferes with Human Immunodeficiency Virus Type 1 Replication," *Microbiol. Immunol.* 46(11):809-817 (2002).

Yamamoto et al., "Inhibition of transcription by the TAR RNA of HIV-1 in a nuclear extract of HeLa cells," *Nucl. Acids Res.* 25(17):3445-3450 (1997).

Yang et al., "Specific Double-Stranded RNA Interference in Undifferentiated Mouse Embryonic Stem Cells," *Mol. Cell. Biol.* 21(22):7807-7816 (2001).

Yarney et al., "Molecular cloning and expression of the ovine testicular follicle stimulating hormone receptor," *Mol. Cell Endroc.* 93:219-226 (1993).

Yee et al., "Prospects for Gene Therapy Using HIV-Based Vectors," *Somatic Cell and Molecular Genetics* 26(1/6):159-173 (2001).

Yu et al., "Progress towards gene therapy of HIV infection," *Gene Therap.* 1:13-26 (1994).

Zakharyan et al., "Stimulation of double-spiral RNA Transformation of Prokaryotic and eukaryotic cells," *Doklady Akadem: Nauk SSR* 288:1251-1253 (1986).

Zamore et al., "RNAi: Double-Stranded RNA Directs the ATP-Dependent Cleavage of mRNA at 21 to 23 Nucleotide Intervals," *Cell* 101:25-33 (2000).

Zernika-Goetz, "Jumping the gun on mouse gene expression," *Nature* 405:733 (Jun. 2000).

Zernicka-Goetz et al., "Following cell fate in the living mouse embryo," *Development* 124:1133-1137 (1997).

Zhang et al., "Single Processing Center Models for Human Dicer and Bacterial RNase III." Cell 2004, vol. 118:57-68.

Zhao et al., "Generating loss-of-function phenotype of the*fushi tarazu* gene with a targeted ribozyme in *drosophila*," *Nature* 365:446-451 (1993).

Zhenhua et al., "Expression of Firefly Luciferase Gene in *Xenopus laevis* oocyte," *Chinese J. Biotech.* 7:279-284 (1991).

Alvarado et al., "Double-stranded RNA specifically disrupts gene expression during planarian regeneration," *Proc. Natl. Acad., Sci. USA*, 1999; 96:5049-5054.

Amirthalingam et al., "Embryonic expression and DNA-binding properties of zebrafish pax-6," *Biochem Biophys Res Commun.*, 1995; Oct 4; 215(1):122-8.

Angell et al., "Consistent gene silencing in transgenic plants expressing a replicating potato virus X RNA," *EMBO J.*, 1997;16(12):3675-3684.

Bahramian et al., "Transcriptional and Posttranscriptional Silencing of Rodent α1(1) Collagen by a Homologous Transcriptionally Self-Silenced Transgene," *Molecular and Cellular Biology*, Jan. 1999;19(1): 274-283.

Barstead, "Genome-wide RNAi," *Curr Opin Chem Biol.*, Feb. 2001; 5(1):63-6.

Baulcombe, "RNA silencing. Diced defence," *Nature*, Jan. 18, 2001; 409(6818): 295-6.

Baulcombe, David C., "Gene Silencing: RNA makes RNA makes no protein," *Current Biology*, 1999;9: R599-R601.

Baulcombe, David C., "Mechanisms of Pathogen-Derived Resistance to Viruses in Transgenic Plants," *The .Plant Cell*, Oct. 1996;8: 1833-1844.

Baulcombe et al., "Ectopic pairing of homologous DNA and post-transcriptional gene silencing in transgenic plants," *Plant Biotechnology*, 1996;7; 173-180.

Benfey et al., "Regulated Genes in Transgenic Plants," *Science*,Apr. 14, 1989;244: 174-181.

Bernstein et al., "Role for a bidentate ribonuclease in the initiation step of RNA interference," *Nature*. Jan. 18, 2001; 409(6818):363-6.

Bosher et al., "RNA interference: genetic wand and genetic watchdog," *Nature Cell Biol.*, Feb. 2000; 2(2):E31-E36.

Branch, Andrea D., "A good antisense molecule is hard to find," *Trends in Biochem. Sci.*, Feb. 1998;23:45-50.

Bruening, G., "Plant gene silencing regularized," *Prc. Natl. Acad. Sci. USA*, Nov. 1998;95: 13349-13351.

Caplen et al., "Specific inhibition of gene expression by small double-stranded RNAs in invertebrate and vertebrate systems," *Proc Natl Acad Sci USA*, Aug. 14, 2001; 98(17):9742-7.

Caplen et al., "dsRNA-mediated gene silencing in cultured *Drosophila* cells: a tissue culture model for the analysis of RNA interference," *Gene*, 2000; 252:95-105.

Cartea et al., "Comparison of sense and antisense methodologies for modifying the fatty acid composition of *Arabidopsis thaliana* oilseed," *Plant Science*, 1998;136: 181-194.

Carthew, "Gene silencing by double-stranded RNA," *Curr Opin Cell Biol.*, Apr. 2001; 13(2):244-8.

Cogoni et al., Gene silencing in *Neurospora crassa* requires a protein homologous to RNA-dependent RNA polymerase, *Nature*, May 13, 1999; 399: 166-169.

Crooke, Stanley T., *Antisense Research and Application*, Published by Springer-Verlag, Chapter 1: 1-50.

Crystal Ronald G., "Transfer of Genes to Humans: Early Lessons and Obstacles to Success," *Science*, 1995; 270: 404-410.

Depraetere, "Biotechnology: If in doubt, interfere," [online]. *Nature News Service: science update*, Jan. 4, 2004. Retrieved from the Internet: <URL:helix.nature.com/nsu/000106/000106-5.html> 2 pgs.

Ding et al., "Cell-to-Cell movement of potato spindle tuber viroid," *The Plant Journal*, 1997;12: 931-936.

Dougherty et al., "Transgenes and gene suppression: telling us something new?," *Current Opinion in Cell Biology*, 1995;7: 399-405.

Elbashir et al., "Duplexes of 21-nucleotide RNAs mediate RNA interference in cultured mammalian cells," *Nature*, May 24, 2001;411(6836): 494-498.

Fire et al., "Potent and specific genetic interference by double-stranded RNA in *Caenorhabditis elegans*," *Nature*, 1998; 391:806-811.

Fire, "RNA-triggered gene silencing," *Trends Genet.*, 1999; 15(9)358-363.

Fire et al., "Production of antisense RNA leads to effective and specific inhibition of gene expression in C. elegans muscle," *Development*, 1991;113:.503-514.

Flavell, R.B., "Inactivation of gene expression in plants as a consequence of specific sequence duplication," *Proc. Natl. Acad. Sci. USA*, Apr. 1994;91: 3490-3496.

Friedmann, "Overcoming the Obstacles," *Scientific American*, Jun. 1997: 96-101.

Gale et al., "Translational Control of Viral Gene Expression in Eukaryotes," *Microbiology and Molecular Biology Reviews*, Jun. 2000;64: 239-280.

Ghislain et al., "The Interferon-Inducible Stat2:Stat1 Heterodimer Preferentially Binds In Vitro to a consensus Element Found in the Promoters of a Subset of Interferon-Stimulated Genes," *J of Interferon Cyrokine Res.*, 2001;21: 379-388.

Grant, Sarah R., "Dissecting the Mechanisms of Posttranscriptional Gene Silencing: Divide and Conquer," *Cell*, Feb. 5, 1999;96: 303-306.

Grishok et al., "Genetic Requirements for Inheritance of RNAi in *C. elegans*," *Science*, Mar. 31, 2000; 287(5462):2494-2497.

Guo et al., "par-1, a Gene Required for Establishing Polarity in *C. elegans* Embryos, Encodes a Putative Ser/Thr Kinase That Is Asymmetrically Distributed," *Cell*. May 19, 1995; 81:611-620.

Halpern et al., "Induction of Muscle Pioneers and Floor Plate is Distinguished by the Zebrafish *no tail* Mutation," *Cell* 1993;75:99-111.

Halpern et al. "Genetic Interactions in Zebrafish Midline Development," *Dev. Biol.*, 1997; 187;154-170.

Hamilton et al., "A species of Small Antisense RNA in Post-transcriptional Gene Silencing in Plants," *Science*, Oct. 29, 1999;286:950-952.

Hamada et al., "Co-suppression of the hydrophobin gene *Hcf-1* is correlated with antisense RNA biosynthesis in *Cladosporium fulvum*," *Mol Gen Genet.*, 1998;259: 630-638.

Hammond et al., "Post-transcriptional gene silencing by double-stranded RNA," *Nat Rev Genet*, Feb. 2001; 2(2):110-9.

Hartmann et al., "Activation of 2'-5' Oligoadenylate Synthetase by Single-stranded and Double-stranded RNA Aptamers," *Journal of Biological Chem.*, Feb. 6, 1998;273(6): 3236-3246.

Herrmann et al., "Cloning of the *T* gene required in mesoderm formation in the mouse," *Nature*, 343:617-622 (1990).

Jordanov et al., "Activation of NF-kB by double-stranded RNA (dsRNA) in the absence of protein kinase R and RNase L demonstrates the existence of two separate dsRNA-triggered antiviral programs." *Mol Cell Biol.*, Jan. 2001; 21(1):61-72.

Jaramillo et al., "The Interferon System: A review with Emphasis on the Role of PKR in Growth Control," *Cancer Invest.*, 1995;13(3)_: 327-338.

Jensen et al., "Cosuppression of *I* Transposon Activity in Drosophila by *I*-Containing Sense and Antisense Transgenes," *Genetics*, Dec. 1999;153; 1767-1774.

Jorgensen et al., "An RNA-Based Information Superhighway in Plants," *Science*. Mar. 6, 1998;279: 1486-1487.

Katze, "Regulation of the Interferon-Induced PKR: can viruses cope?". Trends in Microbiology. vol. 3, No. 2, Feb. 1995. pp. 75-78.

Kaufman, "Double-stranded RNA-activated protein kinase mediates virus-induced apoptosis: a new role for an old actor," *Proc Natl Acad Sci USA.*, Oct. 12, 1999; 96(21):11693-5.

Kennerdell et al., "Use of dsRNA-Mediated Genetic Interference to Demonstrate that *frizzled* and *frizzled 2* Act in the Wingless Pathway," *Cell*, 1998; 95:1017-1026.

Ketting et al., "*mut-7* of *C. elegans*, Required for Transposon Silencing and RNA Interference, Is a Homolog of Werner Syndrome Helicase and RnaseD," *Cell*, Oct. 16, 1999;99: 133-141.

King et al., "STAT1 is inactivated by a caspase," *Biol Chem.*, Apr. 10, 1998; 273(15):8699-704.

Kooter et al., "Listening to the silent genes: transgene silencing, gene regulation and pathogen control," *Trends in Plant Science*, Sep. 1999;4(9): 340-347.

Kumagai et aL, "Cytoplasmic inhibition of carotenoid biosynthesis with virus-derived RNA," *Proc. Natl. Acad. Sci. USA*, Feb. 1995;92: 1679-1683.

Kumar et al., "Antisense RNA: Function and Fate of Duplex RNA in Cells of Higher Eukaryotes," *Microbiol. Mol. Biol. Rev.*, 1998; 62(4):1415-1434.

Lau et al., "Embryonic XMab2112 expression is required for gastrulation and subsequent neural development," *Biochem Biophys Res, Commun.*, Feb. 9, 2001; 280(5):1378-84.

Lee et al., "A Molecular Titration Assay to Measure Transcript Prevalence Levels," *Methods in Enzymology*, 1987; 152:633 & 643.

Li et al., "Double-Stranded RNA Injection Produces Null Phenotypes in Zebrafish," *Dev. Biol.* 217(2):394-405 (available in print Jan. 15, 2000; published electronically Jan. 11, 2000).

Li et al., "*Erratum*" of *Dev Biol* 2000 Jan 15:217(2):394-405, appears in *Dev. Biol.*, 2000 Apr. 15; 220(2):432.

Li et al., "Induction of necrotic-like cell death by tumor necrosis factor alpha and caspase inhibitors: novel mechanism for killing virus-infected cells," *J. Virol.*, Aug. 2000; 74(16):7470-7.

Li et al., "The RelA(p65) subunit of NF-kB is essential for inhibiting double-stranded RNA-induced cytotoxicity," *J. Biol Chem.*, Jan. 12, 2001; 276(2):1185-94.

Liebhaber et al., "Translation inhibition by an mRNA coding region secondary structure is determined by its proximity to the AUG initiation codon," *J. Mol Biol.*, Aug. 5, 1992; 226(3):609-21.

Lindbo et al., "Induction of a Hightly Specific Antiviral State in Transgenic Plants: Implications for Regulation of Gene Expression and Virus Resistance," *The Plant Cell*, Dec. 1993;5; 1749-1759.

Matzke et al., "Epigenetic silencing of plant transgenes as a consequence of divers cellular defence responses," *Cell Mol Life Sci*, 1998;54: 94-103.

Melby et al., "Spatial Regulation of *floating head* Expression in the Developing Notochord," *Dev. Dyn.*, 1997; 209(2):156-165.

Metzlaff et al., "RNA-Mediated RNA Degradation and Chalocone Synthase A Silencing in Petunia," *Cell*, Mar. 21, 1997;88:845-854.

Misquitta et al., "Targeted disruption of gene function in Drosophila by RNA interference (RNA-i): A role for *nautilus* in embryonic somatic muscle formation," *Proc. Natl Acad. Sci. USA*. Feb. 1999;96: 1451-1456.

Montgomery et al., "RNA as a target of double-stranded RNA-mediated genetic interference in *Coenorhabditis elegans*," *Proc. Natl. Acad. Sci. USA*, 95:15502-15507 (1998).

Montgomery et al., "Double-stranded RNA as a mediator in sequence-specific genetic silencing and co-suppression," *Trends Genet.*, 1998; 14(7):255-258.

National Center for Biotechnology Information, National Library of Medicine, National Institutes of Health, GenBank Locus NM_030627, Accession No. NM_030621, "*Homo sapiens* Dicer1, Dcr-1 homolog (Drosophila) (Dicer1), transcript variant 2, mRNA" [online]. Bethesda, MD [retrieved on Dec. 19, 2003]. Retrieved from the Internet:<URL:www.ncbi.nlm.nih.gov/entrez/query.fcgi?cmd=Retreive&db=nucleotide&list_uids=29294648&dopt=GenBank&term=NM_030621&qry=1>; 9 pgs.

National Center for Biotechnology Information, National Library of Medicine, National Institutes of Health, GenBank Locus NM_148948, Accession No. NM_148948, "Mus musculus Dicer1. Dcr-1 homolog (Drosophila) (Dicer1), mRNA," [online]. Bethesda, MD [retrieved on Dec. 19, 2003]. Retrieved from the Internet: <URL:www.ncbi.nlm.nih.gov/entrez/query.fcgi?cmd=Retreive&db=nucleotide&list_uids=22507358&dopt=GenBank&term=NM_148948 &qry=1>; 6 pgs.

National Center for Biotechnology Information, National Library of Medicine, National Institutes of Health, GenBank Locus NM_003733, Accession No. NM_ 003733, "Homo sapiens 2'-5'-oligoadenylate synthetase-like (OASL). transcript variant I, mRNA,"

[online]. Bethesda, MD [retrieved on Dec. 19, 2003]. Retrieved from the Internet:<URL:www.ncbi.nlm.nih.gov/entrez/query.fcgi?cmd=Retreive&db=nucleotide&list_uids=38016933&dopt=GenBank&term=NM_003733&qty=1>; 4 pgs.

National Center for Biotechnology Information, National Library of Medicine, National Institutes of Health, GenBank Locus HUMP68A, Accession No. M35663, "Human p68 kinase mRNA, complete cds.," [online]. Bethesda, MD [retrieved on Dec. 19, 2003]. Retrieved from the Internet:<URL:www.ncbi.nlm.nih.gov/entrez/query.fegi?cmd=Retreive&db=nucleotide&list_uids=189505&dopt=GenBank&term=M35663&qry=1>; 3 pgs.

National Center for Biotechnology Information, National Library of Medicine. National Institutes of Health, GenBank Locus XM_010893, Accession No. XM_010893, "Homo sapiens signal transducer and activator of transcription 1, 91kD (STAT1), mRNA," [online]. Bethesda, MD [retrieved on Dec. 19, 2003]. Retrieved from the Internet:URL:www.ncbi.nlm.nih.gov/entrez/query.fcgi?cmd=Retreive&db=nucleotide&list_uids=205338048&dopt=GenBank&term=NM_010893&qry=1>; 4 pgs.

National Center for Biotechnology Information, National Library of Medicine, National Institutes of Health, GenBank Locus S72725, Accession No. S72725, "E2/NS1=envelope glycoprotein [hepatitis C virus HCV, agammaglobulinemic patient isolate, Genomic RNA, 441 nt]," [online]. Bethesda, MD [Dec. 19, 2003]. Retrieved from the Internet<URL:www.ncbi.nim.nih.gov/entrez/query.fcgi?cmd=Retreive&db=nucleotide&list_uids=619405&dopt=GenBank&term=S72725&qty=1>;2 pgs.

Ngô et al., "Double-stranded RNA induces mRNA degradation in *Trypanosoma brucei*," *Proc. Natl. Acad. Sci. USA*, 1998; 95(25):14687-14692.

Nishikawa et al., "Targeted disruption of a pupal hemocyte protein of Sarcophaga by RNA interference," *Eur J Biochem.*, Oct. 2001; 268(20):5295-9.

Nüsslein-Volhard, "Of Flies and Fishes," *Science*, 1994; 266(5185):572-574.

Oates et al., "Too much interference: injection of double-stranded RNA has nonspecific effects in the zebrafish embryo," *Dev. Biol.*, Aug. 1, 2000; 224(1):20-8.

Pachuk et al., "DNA vaccines-challenges in delivery," *Current Opinion in Molecular Therapeutics*, 2002;2(2): 188-198.

Pachuk et al. "Characterization of a new class of DNA delivery complexes formed by the local anesthetic bupivacaine," *Biochem. Biophys. Acta*, 2000;1468: 20-30.

Paddison et al., "Stable Suppression of gene expression by RNAi in mammalian cells," *Proc Natl Acad Sci USA*, Feb. 5, 2002;99(3): 1443-1448.

Palauqui et al., "Systemic acquired silencing: transgene-specific post-transcriptional silencing is transmitted by grafting from silenced stocks to non-silenced scions," *The EMBO Journal*, 1997;16(15); 4738-4745.

Pelletier et al., "Photochemical cross-linking of cap binding proteins to eucaryotie mRNAs: effect of mRNA 5' secondary structure," *Mol Cell Biol.*, Nov. 1995; 5(11):3222-30.

Proud, "PKR: a new name and new roles". Trends in Biochemical Sciences. Jun. 1995, vol. 20, No. 6, pp. 241-246.

Ratcliff et al., "A similarity Between Viral Defense and Gene Silencing in Plants," *Science*, 1997;276: 1558-1560.

Rocheleau et al., "Wnt Signaling and an APC-Related Gene Specify Endoderm in Early *C. elegans* Embryos," *Cell*, 1997; 90:707-716.

Romano et al., "Inhibition of Double-Stranded RNA-Dependent Protein Kinase PKR by Vaccinia Virus E3: Role of Complex Formation and the E3 N-Terminal Domain," *Molecular and Cellular Biology*, Dec. 1998;18(12): 7304-7316.

Ruiz et al., "Homology-dependent Gene Silencing in *Paramecium*," *Molecular Biology of the Cell*, Apr. 1998;9:931-943.

Ruiz et al., "Initiation and Maintenance of Virus-Induced Gene Silencing," *The Plant Cell*, Jun. 1998;10:937-946.

Russell et al., "Double-stranded RNA triggers generalized translational arrest in *Xenopus oocytes*," *Biochem. Biophys. Res. Comm.*, 1993; 194(2):892-900.

Schiebel et al., "Isolation of an RNA-Directed RNA Polymerase-Specific CDNA Clone from Tomato." *The Plant Cell*, Dec. 1998;10:2087-2101.

Schofield et al., "Non-viral approaches to gene therapy," *British Medical Bulletin*. 1995;51(1): 56-71.

Schulte-Merker et al., "The protein product of the zebrafish homologue of the mouse *T* gene is expressed in nuclei of the germ ring and the notochord of the early embryo," *Development*, Dec. 1992; 116(4):1021-32.

Schulte-Merker et al., "*no. tail* (*ntl*) is the zebrafish homologue of the mouse *T(Brachyury)* gene," *Development*, Apr. 1994; 120(4):1009-15.

Sharp et al., "RNA Interference," *Science*, Mar. 31, 2000; 287(5462):2431-2433.

Smalheiser, et al., "RNAi and brain function: was McConnell on the right track?" *Trends Neurosci.*, Apr. 2001; 24(4):216-8.

Smyth, "Gene silencing: Cosuppression at a distance," *Curr. Biol.*, 1997; 7(12:R793-795.

Starn et al., "Post-transcriptional Silencing of Chalcone Synthase in Petunia by Inverted Transgene Repeats," *The Plant Cell*. 1997:12(1):63-82.

Svoboda et al., "Selective reduction of dormant maternal mRNAs in mouse oocytes by RNA interference," *Development*, 2000; 127:4147. 4155.

Tabara et al., "RNAi in *C. elegans*: Soaking in the Genome Sequence," *Science*, 1998; 282(5388):430-431.

Tabara et al., "The *rde-l* Gene, RNA interference, and Transposon Silencing in *C. elegens*," *Cell*, Oct. 1999;99:123-132.

Timmons et al., "Specific interference by ingested dsRNA," *Nature*, Oct. 1998; 395(6705):854.

Tuschi et al., "Targented mRNA degradation by double-stranded RNA in vitro," *Genes & Development*, 1999;13:3191-3197.

Ui Tei et al., "Sensitive assay of RNA interference in *Drosophila* and Chinese hamster cultured cells using firefly luciferase gene as target," *FEBS Letters*, 2000;479: 79-82.

Vacca, *Laboratory Manual of Histochemistry*, Raven Press, New York, 1985, Title page, publication page, table of contents, and pp. 352-354.

Van Blokland et al., "Transgene-mediated suppression of chalcone synthase expression in *Petunia hybrida* results from an increase in RNA turnover," *The Plant Journal*, 1994;6: 861-877.

Verma et al., "Gene therapy- promises, problems and prospects," *Nature*, Sep. 18, 1997;389:239-242.

Voinnet et al., "Systemic signalling in gene silencing," *Nature*, Oct. 9, 1997;389: 553.

Voinnet et al., "Systemic Spread of sequence-Specific Transgene RNA Degradation in Plants is Initiated by Localized Introduction of Ectopic Promoterless DNA," *Cell*, Oct. 1998;95:177-187.

Wagner et al., "Double-Stranded RNA poses puzzle," *Nature*, 1998;391:744-745.

Wassenegger et al., "A model for RNA-mediated gene silencing in higher plants," *Plant Mol. Biol.*, 1998; 37(2):349-362.

Wassenegger et el., "RNA-directed De Novo Methylation of Genomic Sequences in Plants," *Cell*, Feb. 11, 1994;76:567-576.

Waterhouse et al., "Vitus resistance and gene silencing in plants can be induced by simultaneous expression of sense and antisense RNA," *Proc. Natl. Acad. Sci. USA*, 1998; 95(23):13959-13964.

Weaver et al., "Apoptosis is promoted by the dsRNA-activated factor (DRAF1) during viral infection independent of the action of interferon or p53," *FASEB J*. Feb. 2001; 15(2):501-15.

Westerfield, *The Zebrafish Book: A guide for the laboratory use of zebrafish (Danio rerio)* 3rd edition, [online]. 1993, University of Oregon Press, Eugene, OR. Retrieved from the Internet: <URL:zfish.uoregon.edu/zf%5Finfo/zfbook/zfbk.html>; Title page, Publication page, Table of Contents only, 7 pgs.

Wianny et al., "Specific interference with gene function by double-stranded RNA in early mouse development," *Nature Cell Biol.*, 2:70-75 (available in print Feb. 2000; published electronically Dec. 23, 1999).

Wilkinson, "Whole mount in situ hybridization of vertebrate embryos," In situ *hybridization, a practical approach*, Rickwood et al., eds., IRL Press, Oxford 1992, Title page, publication page, table of contents, and pp. 75-83.

Willett et al., "Expression of zebrafish *rag* genes during early development identifies the thymus," *Dev Biol.*, Feb. 15, 1997;182(2):331-41.

Willert et al., "A *Drosophila* Axin homolog, *Daxin*, inhibits Wnt signaling," *Development*, 1999;126: 4165-4173.

Xie et al., "A ribozyme-mediated. gene "knockdown" strategy for the identification of gene function in zebrafish," *Proc. Natl. Acad. Sci. USA*, 1997; 94(25):13777-13781.

Yeung et al., "Inhibitory role of the host apoptogenic gene PKR in the establishment of persistent infection by encephalomyocarditis virus in U937 cells," *Proc Natl Acad Sci USA*, Oct. 12, 1999; 96(21):11860-5.

Zamore, "RNA interference: listening to the sound of silence.," *Nat Struct Biol.*, Sep. 2001; 8(9):746-50.

Zhao et al., "Double-Stranded RNA Injection Produces Nonspecific Defects in Zebrafish," *Developmental Biology*, 2001; 229:215-223.

Agami, "RNAi and related mechanisms and their potential use for therapy," *Current Opinion in Chemical Biology*, 2002, vol. 6:829-834.

Agrawal et al., "Antisense Therapeutics: is it as simple as complementary base recognition?." *Molecular Medicine Today*, 2000, vol. 6:72-81.

Caplen, "RNAi as a gene therapy approach," *Expert Opin. Biol. Ther.* 2003, vol. 3:75-586.

Check, "RNA to the rescue?," *Nature*, 2003, vol. 425:10-12.

Coburn et al., "siRNAs: a new wave fo RNA-based therapeutics," *Journal of Antimicrobial Chemotherapy* 2003, vol. 51:753-756.

Flanagan et al., "Cellular penetration and antisense activity by a phenoxazine-substituted heptanucleotide," *Nature Biotechnology*. 1999, vol. 17:48-52.

Green et al., "Antisense Oligonucleotides: an evolving technology for the modulation of gene expression in human disease," *J. Am. Coll. Surg.* 2000, vol. 191:93-105.

Jen et al., "Suppression of gene expression by targeted disruption of messenger RNA: available options and current strategies," *Stem Cells* 2000, vol. 18:307-319.

Opalinska et al. "Nucleic-Acid Therapeutics: Basic Principles and Recent Applications," *Nature Review*, 2002, vol. 1:503-514.

Wang et al., "Progress in the Delivery of Therapeutic Oligonucleotides: Organ/Cellular Distribution and Targeted Delivery of Oligonncleotides In Vivo," *Antisense and Nucleic Acid Drug Delivery*, 2003, vol. 13:169-189.

Zhang et al., "Targeted Gene Silencing by Small Interfering RNA-Based Knock-Down Technology," *Current Pharmaceutical Biotechnology*, 2004, vol. 5:1-7.

Adams, "RNA Therapeutics Enter Clinical Trials," (2005) The Scientist, vol. 19, Issue 1, Retreived from the Internet on Jan. 18, 2005, Retreived as http://www.the-scientist.com/2005/1/17/28/1 6 pages.

Andino, "RNAi puts a lid on virus replication," (2003) Nature Biotechnology, vol. 21, No. 6, pp. 629-630.

Caplen, "RNAi quashes polyQ," (2004) Nature Medicine, vol. 10, No. 8, pp. 773-776.

Check, "Hopes rise for RNA therapy as mouse study hits target," (2004) Nature, vol. 432, p. 136.

Dorland's Illustrated Medical Dictionary, (2000) 29th Edition, p. 1140.

Heidel et al., "Lack of interferon response in animals to naked siRNAs," (2004) Nature Biotechnology, vol. 22, No. 12, pp. 1579-1582.

McCaffrey et al., "RNA Interference in Adult Mice," (2002) Nature, vol. 418, pp. 38-39.

McCaffrey et al., "Inhibition of hepatitis B virus in mice by RNA interference," (2003). Nature Biotechnology, vol. 21, No. 6, pp. 639-644.

*News Release*, "Acuity Pharmaceuticals Closes $15 Million Financing and Initiates First-Ever Clinical Trial of an RNAi Therapeutic, " Philadelphia, Oct. 7/PRNewswire, retrieved from the Internet. Retrived as http://www.biospace.com/news_story.cfm?StoryID=17599420&full=1 (1 of 3)Jan. 31, 2005 11:10:52 a.m.

*News Release*. Sirna Therapeutics. "Sirna Therapeutics Commences Phase I Clinical Trial for Age-Related Macular Degeneration at Cleveland Clinic," Boulder, Colo., Nov. 23/PRNewsire. Retrieved from the Internet. Retrieved as http://phx.corporate-ir.net/phoenix.zhtml?c=141787&p=irol-newsArticle&ID=6468308&highlight= (1 of 4) Jan. 31, 2005 11:16:03 AM, 4 pages.

*News Release*. Sirna Therapeutics. "Sirna Therapeutics and Targeted Genetics Form Huntington's Disease Collaboration, " Boulder, Colo. and Seattle, Jan. 11/PRNewswire. Retrieved from the Internet. Retrieved as http://phx.corporate-ir.net/phoenix.zhtml?c=141787&p=irol-newsArticle&ID=1661337&highlights= (1 of 4) Jan. 31, 2005 11:14:20 AM, 4 pages.

Rossi. "A Cholesterol Connection in RNAi," (2004) Nature, vol. 432, pp. 155-156.

Soutschek et al., "Therapeutic silencing of an endogenous gene by systemic administration of modified siRNAs," (2004) Nature, vol. 432, pp. 173-178.

ZFIN—The Zebrafish Model Organism Database. Database Information Sheet. Copyright © University of Oregon, 1994-2005, Eugene, Oregon. Retrieved from the Internet on Mar. 7, 2005. http://zfin.org/zf_info/dbase/db.html, 2 pages.

Xi et al., "RNAi suppresses polyglutamine-induced neurogeneration in a model of spinocerebellar ataxia, " (2004) Nature Medicine, vol.10, No. 8, pp. 816-820.

Conklin. "RNA Interference-Based Silencing of Mammalian Gene Expression, " *ChemBioChem* 2003, 4:1033-1089.

Ngo et al., "Double-Stranded RNA Induces mRNA Degradation in *Trypanosoma brucei*" Proc. Natl. Acad. Sci. USA 95:14687-14692 (1998).

Caplen et al., dsRNA-mediated gene silencing in cultured *Drosophila* cells: a tissue culture model for the analysis of RNA interference, 2000. Gene 252:95-105.

Doan et al., "High-throughput target validation in model organisms," 2004. *DDT: Targets*, 3(5):191-197.

Liu et al., "Efficient RNA interference in zebrafish embryos using siRNA synthesized with SP6 RNA polymerase," 2005. *Develop. Growth Differ*. 47:323-331.

Wang et al., "U6 promoter-driven siRNA injection has nonspecific effects in zebrafish," 2010. *Biochemical and Biophysical Research Communications*, 391:1363-1368.

dsRNA effect on Mice NIH/3T3 Cell Line

SEQUENCE LISTING

```
<160> NUMBER OF SEQ ID NOS: 20

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence:    primer

<400> SEQUENCE: 1
ttggaacaac ttgagggtga                                                      20

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence:    primer

<400> SEQUENCE: 2
cggtcacttt tcaaagcgta t                                                    21

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence:    primer

<400> SEQUENCE: 3
accctataca cccccacctc                                                      20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence:    primer

<400> SEQUENCE: 4
ataataggca ccgctcatgc                                                      20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence:    primer

<400> SEQUENCE: 5
ttttcgaggt tcccttgttg                                                      20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence:    primer

<400> SEQUENCE: 6
```

```
agcctttgta tcctcgctga                                              20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence:   primer

<400> SEQUENCE: 7
aaccgtgttt aacgggatca                                              20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence:   primer

<400> SEQUENCE: 8
ggttgcactg gcactaccat                                              20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence:   primer

<400> SEQUENCE: 9
catcttgcat gctgtccact                                              20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence:   primer

<400> SEQUENCE: 10
agatcttcac ccgggtcttc                                              20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence:   primer

<400> SEQUENCE: 11
catttgccaa cacgagtcaa                                              20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence:   primer

<400> SEQUENCE: 12
ccagtccagt gccatttgat                                              20

<210> SEQ ID NO 13
<211> LENGTH: 37
<212> TYPE: DNA
<213> ORGANISM: Artificial Sequence
```

```
<220> FEATURE:
<223> OTHER INFORMATION: Description of Artificial Sequence:   primer

<400> SEQUENCE: 13
taatacgact cactataggg taaacggcca caagttc                              37

<210> SEQ ID NO 14
<211> LENGTH: 37
<212> TYPE: DNA
<213> ORGANISM: Artificial Sequence
<220> FEATURE:
<223> OTHER INFORMATION: Description of Artificial Sequence:   primer

<400> SEQUENCE: 14
taatacgact cactataggg tcgtgctgct tcatgtg                              37

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence:   primer

<400> SEQUENCE: 15
ttgatcttgg cttcaggagg                                                 20

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence:   primer

<400> SEQUENCE: 16
tgcaatggtt accagttttg a                                               21

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence:   primer

<400> SEQUENCE: 17
cccttgactt tgagcaggag                                                 20

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence:   primer

<400> SEQUENCE: 18
acaggtcctt acggatgtcg                                                 20

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence:   primer

<400> SEQUENCE: 19
tctgcaccag cattagcact                                                 20
```

```
<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence:  primer

<400> SEQUENCE: 20
tgctgtgaga attcgactgg                                                  20
```

COMPOSITION AND METHOD FOR IN VIVO AND IN VITRO ATTENUATION OF GENE EXPRESSION USING DOUBLE STRANDED RNA

This application is a continuation of application Ser. No. 10/772.661, filed Feb. 5, 2004, which is a continuation of application Ser. No. 10/038,984 filed Jan. 4, 2002, which is a continuation of application Ser. No. 09/493,301, filed Jan. 28, 2000, which claims the benefit of U.S. Provisional Application Ser. No. 60/117,635, filed Jan. 28, 1999 and U.S. Provisional Application Ser. No. 60/175,440, filed Jan. 11, 2000, all of which are incorporated by reference.

STATEMENT OF GOVERNMENT RIGHTS

This invention was made with government support under grants from the United States Public Health Service, Grant Nos. HL36059, HL51533, and HD17063. The U.S. Government has certain rights in this invention.

BACKGROUND OF THE INVENTION

Double-stranded RNA has been shown to attenuate specific gene expression in *C. elegans, Drosophila* and *Trypanosoma brucei* (M. Montgomery, et al., *Proc. Natl. Acad. Sci. USA*. 95, 15502-15507 (1998); J. Kennerdell et al., *Cell* 95, 1017-1026 (1998); H. Ngo et al., *Proc. Natl. Acad. Sci. USA*. 95, 14687-14692 (1998)). The types of genes attenuated in these invertebrates include some encoding transcription factors and others that encode growth factor receptors. There is also evidence that double-stranded RNA may effectively silence gene expression in plants (M. Wassenegger et al., *Plant. Mol. Biol.* 37, 349-362 (1998); P. Watergiyse et al., *Proc. Natl. Acad. Sci. U.S.A.* 95, 13959-13964 (1998)). Application of this method to vertebrates would be an extremely useful tool for the study of vertebrate developmental genetics and has numerous medical implications as well, however researchers have heretofore been unable to obtain successful gene silencing in vertebrates using this method.

A definitive mechanism through which double-stranded RNA effects gene silencing remains has not been identified (M. Montgomery et al., *Trends Genet.* 14, 255-258 (1998)). Recently, Montgomery et al. reported that double-stranded RNA induces specific RNA degradation in nematodes (*Proc. Natl. Acad. Sci. U.S.A.* 95, 15502-15507 (1998)). This conclusion was based upon the fact that DNA sequences in the targeted regions of the gene were not altered and that 100% of the F2 generation reverted to the wild type phenotype. In addition, *C. elegans* has a unique genetic organization. Genes in this animal are organized in operons in which a single promoter controls expression of a number of genes. They showed that the double-stranded RNA affects only expression of the targeted gene. In contrast, however, others have observed heritable effects of double-stranded RNA on the expression of a number of genes in *C. elegans*, suggesting that more than one mechanism may be involved in double-stranded RNA-mediated inhibition of gene activity (H. Tahara, *Science* 28, 431-432 (1998)).

In transgenic plants, co-suppression of gene expression can be mediated through rapid degradation of the mRNA produced by the targeted gene (D. Smyth, *Curr. Biol.* 7, R793-795 (1997)). Others have shown that double-stranded RNA-dependent sequence-specific methylation may mediate the long-term effects of co-suppression in plants. Such a methylase may also be dependent on transcription of the targeted sequence since double-stranded RNA targeted to promoter regions in nematode had no apparent effect on transcription.

SUMMARY OF THE INVENTION

The present invention provides a method for attenuating gene expression in a cell using gene-targeted double-stranded RNA (dsRNA). The dsRNA contains a nucleotide sequence that is essentially identical to the nucleotide sequence of at least a portion of the target gene. The cell into which the dsRNA is introduced can be derived from or contained in any organism (e.g., plant, animal, protozoan, virus, bacterium, or fungus). Gene expression can be attenuated in a whole organism, an organ or tissue of an organism, including a tissue explant, or in cell culture. Preferably, the cell is a vertebrate cell, but the invention is not limited to vertebrates. Double-stranded RNA is introduced directly into the cell or, alternatively, into the extracellular environment from which it is taken up by the cell. Inhibition is specific for the targeted gene. The targeted gene can be a chromosomal gene or an extrachromosomal gene. For example, the targeted gene may be present in the genome of the cell into which the dsRNA is introduced, or in the genome of a pathogen, such as a virus, a bacterium, a fungus of a protozoan, which is capable of infecting such cell. The targeted gene can be an endogenous gene or a foreign gene. Depending on the particular target gene and the dose of dsRNA delivered, the method may partially or completely in inhibit expression of the gene in the cell. The expression of two or more genes can be attenuated concurrently by introducing two or more double stranded RNAs into the cell in amounts sufficient to attenuate expression of their respective target genes. Double stranded RNAs that are administered "concurrently" are administered, together or separately, so as to be effective at generally the same time.

In another aspect, the invention provides a method for attenuating the expression of a target gene in an organism that involves introducing a double stranded RNA into an embryo in an amount sufficient to attenuate expression of the target gene, then growing the embryo into a fully developed organism, e.g., an adult organism, in which expression of the target gene is attenuated. Optionally, a phenotypic change in the organism associated with attenuated expression of the target gene can be identified.

In another aspect, the invention provides a method for attenuating the expression of a target gene in a tissue explant that involves explanting a tissue from an organism then introducing a double stranded RNA into a cell of the tissue explant in an amount sufficient to attenuate expression of the target gene. Optionally, the tissue explant exhibiting attenuated expression of the target gene is implanted back into the organism or is implanted into a different organism. Also optionally, a phenotypic change in the tissue explant associated with attenuated expression of the target gene can be identified.

In yet another aspect, the invention provides a method for attenuating the expression of a target gene in a cell that includes annealing two complementary single stranded RNAs in the presence of potassium chloride to yield double stranded RNA; contacting the double stranded RNA with RNAse to purify the double stranded RNA by removing single stranded RNA; and introducing the purified double stranded RNA into the cell in an amount sufficient to attenuate expression of the target gene.

The invention further provides a method for treating or preventing a disease or infection in a mammal. Double stranded RNA is administered to the mammal in an amount sufficient to attenuate expression of a target gene, the expression of which is associated with the disease or infection. The method can be used to treat or prevent a viral infection, in which case the double stranded RNA is an antiviral double stranded RNA that attenuates the expression of a viral gene. Alternatively, the method can be used to treat or prevent cancer, in which case the double stranded RNA is an antitumor double stranded RNA, or to treat an autosomal dominant genetic disease such as Huntington's chorea, in which case the double stranded RNA attenuates the expression of an allele of a gene that is associated with the disease. Concurrent inhibition of multiple genes is advantageous to treat diseases associated with multiple genes, or to treat two or more diseases or infections concurrently.

The method of the invention can further be used to reduce or prevent the rejection response to transplant tissue. A double stranded RNA that attenuates the expression of a gene in the transplant tissue that can elicit an immune response in the recipient is administered to the transplant tissue. Preferably, the transplant tissue is hepatocytes.

Also provided by the invention is a vertebrate cell that contains a double stranded RNA having a nucleotide sequence that is essentially identical to the nucleotide sequence of at least a portion of a target gene. The vertebrate cell is preferably a fish cell, a murine cell, a bird cell or a human cell. A vertebrate that contains the vertebrate cell of the invention is also provided.

The invention also provides a kit that includes reagents for attenuating the expression of a target gene in a cell. The kit contains a DNA template that has two different promoters (preferably a T7 promoter, a T3 promoter or an SP6 promoter), each operably linked to a nucleotide sequence. Two complementary single stranded RNAs can be transcribed from the DNA template, which can be annealed to form a double stranded RNA effective to attenuate expression of the target gene. The kit optionally contains amplification primers for amplifying the DNA sequence from the DNA template and nucleotide triphosphates (i.e., ATP, GTP, CTP and UTP) for forming RNA. Also optionally, the kit contains two RNA polymerases, each capable of binding to a promoter on the DNA template and causing transcription of the nucleotide sequence to which the promoter is operably linked; a purification column for purifying single stranded RNA, such as a size exclusion column; one or more buffers, for example a buffer for annealing single stranded RNAs to yield double stranded RNA; and RNAse A or RNAse T for purifying double stranded RNA.

DETAILED DESCRIPTION

Figure 1A:
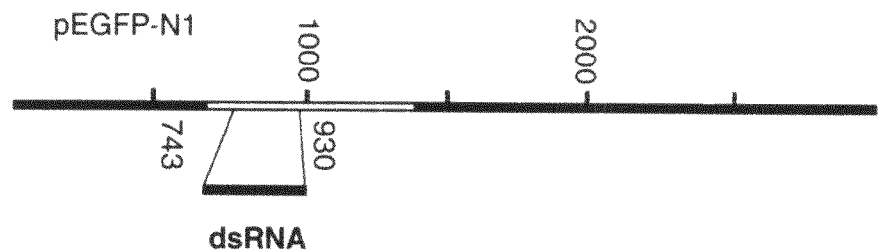
FIG. 1 is a schematic of double-stranded RNA targeted to (a) green fluorescent protein (GFP); (b) Zf-T; or (c) Pax6.1; the location of the sequences that were used as templates to produce the GFP, Zf-T, or Pax6.1 double-stranded RNA are indicated as dsRNA and the starting and ending bases are indicated for each.

The present invention provides a method for gene silencing in organisms and cells, especially vertebrates, using gene-specific double-stranded RNA. The ability to use double-stranded RNA to specifically block expression of particular genes in a multicellular setting both in vivo and in vitro has broad implications for the study of developmental genetics. Equally important, it opens up a host of new medical applications. Examples include the construction of anti-viral agents, anti-tumor agents, and therapeutics designed to block expression of specific alleles of genes that have been implicated in autosomal dominant genetic diseases such as Huntington's chorea. As another example, transplant rejection could be managed prior to transplantation by its vitro incubation of the tissues to be transplanted, such as hepatocytes, with an agent designed to block expression of genes associated with the generation of the host immune response.

The method of the present invention allows for attenuation of gene expression in a cell. "Attenuation of gene expression." can take the form of partial or complete inhibition of gene function. Mechanistically, gene function can be partially or completely in inhibited by blocking transcription from the gene to mRNA, or by blocking translation of the mRNA to yield the protein encoded by the gene, although it should be understood that the invention is not limited to any particular mechanism of attenuation of gene expression. Inhibition of gene function is evidenced by a reduction or elimination, in the cell, of the activity associated with the protein encoded by the gene. Whether and to what extent gene function is inhibited can be determined using methods known in the art. For example, in many cases in inhibition of gene function leads to a change in phenotype which is revealed by examination of the outward properties of the cell or organism or by biochemical techniques such as RNA solution hybridization, nuclease protection, Northern hybridization, reverse transcription, gene expression monitoring with a microarray, antibody binding, enzyme linked immunosorbent assay (ELISA), Western blotting, radioimmunoassay (RIA), other immunoassays, and fluorescence activated cell analysis (FACS). For RNA-mediated inhibition in a cell line or whole organism, gene expression is conveniently assayed by use of a reporter or drug resistance gene whose protein product is easily assayed. Such reporter genes include acetohydroxyacid synthase (AHAS), alkaline phosphatase (AP), beta galactosidase (LacZ), beta glucuronidase (GUS), chloramphenicol acetyltransferase (CAT), green fluorescent protein (GFP), horseradish peroxidase (HRP), luciferase (Luc), nopaline synthase (NOS), octopine synthase (OCS), and derivatives thereof. Multiple selectable markers are available that confer resistance to ampicillin, bleomycin, chloramphenicol, gentamycin, hygromycin, kanamycin, lincomycin, methotrexate, phosphinothricin, puromycin, and tetracyclin.

Attenuation of gene expression can be quantified, and the amount of attenuation of gene expression in a treated cell compared to a cell not treated according to the present invention can be determined. Lower doses dsRNA may result in inhibition in a smaller fraction of cells, or in partial inhibition in cells. In addition, attenuation of gene expression can be time-dependent; the longer the period of time since the administration of the dsRNA, the less gene expression may be attenuated. Attenuation of gene expression can occur at the level of transcription (i.e., accumulation of mRNA of the targeted gene), or translation (i.e., production of the protein encoded by the targeted gene). For example, mRNA from the targeted gene can be detected using a hybridization probe having a nucleotide sequence outside the region selected for the inhibitory double-stranded RNA, and translated polypeptide encoded by the target gene can be detected via Western blotting using an antibody raised against the polypeptide. It should be noted that the method of the invention is not limited to any particular mechanism for reducing or eliminating cellular protein activity; indeed, as noted above, it is not yet fully understood how the introduction of dsRNA into a cell causes attenuation of expression of the targeted gene, nor is it known whether single or multiple mechanisms are at work.

The attenuation of gene expression achieved by the method of the invention is specific for the targeted gene. In other words, the dsRNA inhibits the target gene without manifest effects on other genes of the cell. Additionally, the inhibition of the function of specific genes preferably, although not necessarily, passes through the germline.

Targeted Gene

Any gene being expressed in a cell can be targeted. A gene that is expressed in the cell is one that is transcribed to yield an mRNA and, optionally, a protein. The targeted gene can be chromosomal (i.e., genomic) or extrachromosomal. It may be endogenous to the cell, or it may be a foreign gene (i.e., a transgene). The foreign gene can be integrated into the host genome, or it may be present on an extrachromosomal genetic construct such as a plasmid or a cosmid. The targeted gene can also be derived from a pathogen, such as a virus, bacterium, fungus or protozoan, which is capable of infecting an organism or cell.

The cell containing the target gene may be derived from or contained in any organism (e.g., plant, animal, protozoan, virus, bacterium, or fungus). The plant may be a monocot, dicot or gymnosperm; the animal may be a vertebrate or invertebrate. Preferred microbes are those used in agriculture or by industry, and those that are pathogenic for plants or animals. Fungi include organisms in both the mold and yeast morphologies. Examples of vertebrates include fish and mammals, including cattle, goat, pig, sheep, hamster, mouse, rat, and human; invertebrate animals include nematodes and other worms, *Drosophila*, and other insects. Preferably, the cell is a vertebrate cell.

The cell having the target gene may be from the germ line or somatic, totipotent or pluripotent, dividing or non-dividing, parenchyma or epithelium, immortalized or transformed, or the like. The cell can be a gamete or an embryo; if an embryo, it can be a single cell embryo or a constituent cell or cells from a multicellular embryo. The term "embryo" thus also includes fetal tissue. The cell having the target gene may be an undifferentiated cell, such as a stem cell, or a differentiated cell, such as from a cell of an organ or tissue, including fetal tissue, or any other cell present in an organism. Cell types that are differentiated include adipocytes, fibroblasts, myocytes, cardiomyocytes, endothelium, neurons, glia, blood cells, megakaryocytes, lymphocytes, macrophages, neutrophils, eosinophils, basophils, mast cells, leukocytes, granulocytes, keratinocytes, chondrocytes, osteoblasts, osteoclasts, hepatocytes, and cells of the endocrine or exocrine glands.

Double-Stranded RNA

The dsRNA is formed from one or more strands of polymerized ribonucleotide. When formed from only one strand, it takes the form of a self-complementary hairpin-type molecule that doubles back on itself to form a duplex. When formed from two strands, the two strands are complementary RNA strands. The dsRNA can include modifications to either the phosphate-sugar backbone or the nucleoside. For example, the phosphodiester linkages of natural RNA may be modified to include at least one of a nitrogen or sulfur heteroatom. Likewise, bases may be modified to block the activity of adenosine deaminase.

The nucleotide sequence of the dsRNA is defined by the nucleotide sequence of its targeted gene. The dsRNA contains a nucleotide sequence that is essentially identical to at least a portion of the target gene; preferably the dsRNA contains a nucleotide sequence that is completely identical to at least a portion of the target gene. It should be understood that in comparing an RNA sequence to a DNA sequence, an "identical" RNA sequence will contain ribonucleotides where the DNA sequence contains deoxyribonucleotides, and further that the RNA sequence will contain a uracil at positions where the DNA sequence contains thymidine. More preferably, the dsRNA that is completely identical to at least a portion of the target gene does not contain any additional nucleotides. The portion of the target gene to which the dsRNA sequence is essentially or completely identical is preferably a sequence that is unique to the genome of the cell into which the dsRNA is to be introduced.

A dsRNA that is "essentially identical" to a least a portion of the target gene is a dsRNA wherein one of the two complementary strands (or, in the case of a self-complementary RNA, one of the two self-complementary portions) is either identical to the sequence of that portion of the target gene or contains one or more insertions, deletions or single point mutations relative to the nucleotide sequence of that portion of the target gene. The invention thus has the advantage of being able to tolerate sequence variations that might be expected due to genetic mutation, strain polymorphism, or evolutionary divergence. Alternatively, a dsRNA that is "essentially identical" to at least a portion of the target gene can be functionally as a dsRNA wherein one of the two complementary strands (or, in the case of a self-complementary RNA, one of the two self-complementary portions) is capable of hybridizing with a portion of the target gene transcript (e.g., under conditions including 400 mM NaCl, 40 mM PIPES pH 6.4, 1 mM EDTA, 50° C. or 70° C. hybridization for 12-16 hours; followed by washing).

The dsRNA nucleotide sequence that is essentially or completely identical to at least a portion of the target gene has a length of preferably at least about 25 bases, more preferably at least about 50 bases, and most preferably at least about 100 bases. The dsRNA nucleotide sequence has a length of preferably less than about 400 bases, more preferably less than about 300 base, and most preferably less than about 200 bases. It will be understood that the length of the dsRNA, the degree of homology necessary to affect gene expression, and the most effective dosages can be optimized for each particular application using routine methods.

Synthesis of dsRNA

Single strands of RNA are synthesized in vitro. Preferably, single stranded RNA is enzymatically synthesized from the PCR products of a DNA template, preferably a cloned a cDNA template. Provided the sequence of the target gene is known, a cloned cDNA template can be readily made from target cell RNA using reverse-transcriptase polymerase chain reaction (RT-PCR) to generate a cDNA fragment, following by cloning the cDNA fragment into a suitable vector. Preferably, the vector is designed to allow the generation of complementary forward and reverse PCR products. The vector pGEM-T (Promega, Madison Wis.) is well-suited for use in the method because it contains a cloning site positioned between oppositely oriented promoters (i.e., T7 and SP6 promoters; T3 promoter could also be used). After purification of the PCR products, complementary single stranded RNAs are synthesized, in separate reactions, from the DNA templates via RT-PCR using two different RNA polymerases (e.g., in the case of pGEM-T, T7 polymerase and SP6 polymerase). RNAse-free DNAse is added to remove the DNA template, then the single-stranded RNA is purified. Single strands of RNA can also be produced enzymatically or by partial/total organic synthesis. The use of in vitro enzymatic or organic synthesis allows the introduction of any desired modified ribonucleotide. The RNA strands may or may not be polyadenylated; and the RNA strands may or may not be capable of being translated into a polypeptide by a cell's translational apparatus. Preferably, purification of RNA is performed without the use of phenol or chloroform.

Double stranded RNA is formed in vitro by mixing complementary single stranded RNAs, preferably in a molar ratio of at least about 3:7, more preferably in a molar ratio of about 4:6, and most preferably in essentially equal molar amounts (i.e., a molar ratio of about 5:5). Preferably, the single stranded RNAs are denatured prior to annealing, and the buffer in which the annealing reaction takes place contains a salt, preferably potassium chloride. Prior to administration, the mixture containing the annealed (i.e., double stranded) RNA is preferably treated with an enzyme that is specific for single stranded RNA (for example, RNAse A or RNAse T) to confirm annealing and to degrade any remaining single stranded RNAs. Addition of the RNAse also serves to excise any overhanging ends on the dsRNA duplexes.

Delivery of dsRNA to a Cell

Double stranded RNA can be introduced into the cell in a number of different ways. For example, in the case of an embryo, the dsRNA is conveniently administered by microinjection; other methods of introducing nucleic acids into a cell include bombardment by particles covered by the dsRNA, soaking the cell or organism in a solution of the dsRNA, electroporation of cell membranes in the presence of the dsRNA, liposome-mediated delivery of dsRNA and transfection mediated by chemicals such as calcium phosphate, viral infection, transformation, and the like. The dsRNA may be introduced along with components that enhance RNA uptake by the cell, stabilize the annealed strands, or otherwise increase in inhibition of the target gene. In the case of a cell culture or tissue explant, the cells are conveniently incubated in a solution containing the dsRNA or lipid-mediated transfection; in the case of a whole animal or plant, the dsRNA is conveniently introduced by injection or perfusion into a cavity or interstitial space of an organism, or systemically via oral, topical, parenteral (including subcutaneous, intramuscular and intravenous administration), vaginal, rectal, intranasal, ophthalmic, or intraperitoneal administration. In addition, the dsRNA can be administered via and implantable extended release device. Methods for oral introduction include direct mixing of RNA with food of the organism, as well as engineered approaches in which a species that is used as food is engineered to express an RNA, then fed to the organism to be affected. The dsRNA may be sprayed onto a plant or a plant may be genetically engineered to express the RNA in an amount sufficient to kill some or all of a pathogen known to infect the plant.

Alternatively, dsRNA can be supplied to a cell indirectly by introducing one or more vectors that encode both single strands of a dsRNA (or, in the case of a self-complementary RNA, the single self-complementary strand) into the cell. Preferably, the vector contains 5' and 3' regulatory elements that facilitate transcription of the coding sequence. Single stranded RNA is transcribed inside the cell, and, presumably, double stranded RNA forms and attenuates expression of the target gene. Methods for supplying a cell with dsRNA by introducing a vector from which it can be transcribed are set forth in WO 99/32619 (Fire et al., published 1 Jul. 1999). A transgenic animal that expresses RNA from such a recombinant construct may be produced by introducing the construct info a zygote, an embryonic stem cell, or another multipotent cell derived from the appropriate organism. A viral construct packaged into a viral particle would accomplish both efficient introduction of an expression construct into the cell and transcription of RNA encoded by the expression construct.

The dsRNA is typically administered in an amount that allows delivery of at least one copy per cell. The amount of dsRNA administered to a cell, tissue, or organism depends on the nature of the cell, tissue, or organism, the nature of the target gene, and the nature of the dsRNA, and can readily be optimized to obtain the desired level of gene inhibition. To attenuate gene expression in a single cell embryo, for example, at least about $0.8 \times 10^6$ molecules of dsRNA are injected; more preferably, at least about $20 \times 10^6$ molecules of dsRNA are injected; most preferably, at least about $50 \times 10^6$ molecules of dsRNA are injected. The amount of dsRNA injected into a single cell embryo is, however, preferably at most about $1000 \times 10^6$ molecules; more preferably, it is at most about $500 \times 10^6$ molecules, most preferably, at most about $100 \times 10^6$ molecules. In the case of administration of dsRNA to a cell culture or to cells in tissue, by methods other than injection, for example by soaking, electroporation, or lipid-mediated transfection, the cells are preferably exposed to similar levels of dsRNA in the medium. For example, 8-10 μL of cell culture or tissue can be contacted with about $20 \times 10^6$ to about $2000 \times 10^6$ molecules of dsRNA, more preferably about $100 \times 10^6$ to about $500 \times 10^6$ molecules of dsRNA, for effective attenuation of gene expression.

Once the minimum effective length of the dsRNA has been determined, it is routine to determine the effects of dsRNA agents that are produced using synthesized oligoribonucleotides. The administration of the dsRNA can be by microinjection or by other means used to deliver nucleic acids to cells and tissues, including culturing the tissue in medium containing the dsRNA.

Scientific, Industrial and Medical Applications of the Technology

The present invention may be used to introduce dsRNA into a cell for the treatment or prevention of disease. To treat or prevent a disease or other pathology, a target gene is selected which is required for initiation or maintenance of the disease/pathology. The dsRNA can be introduced into the organism using in vitro, ex vivo or in vivo methods. In an in vitro method, the dsRNA is introduced into a cell, which may or may not be a cell of the organism, and the dsRNA-containing cell is then introduced into the organism. In an ex vivo method, cells of the organism are explanted, the dsRNA is introduced into the explanted cells, and the dsRNA-containing cells are implanted back into the host. In an in vivo method, dsRNA is administered directly to the organism. As noted above, the dsRNA can also be delivered to a cell using one or more vectors that encode the complementary RNAs (or self-complementary RNA), which are men transcribed inside the cell and annealed to yield the desired dsRNA.

In medical applications, the target gene can be an endogenous gene of the organism, or can be the gene of a pathogen. For example, dsRNA may be introduced into a cancerous cell or tumor, and thereby inhibit expression of a gene required for maintenance of the carcinogenic/tumorigenic phenotype. An exemplary list of potential target genes, including developmental genes, oncogenes, and enzymes, and a list of cancers that can be treated according to the present invention can be found in WO 99/32619 (Fire et al., published 1 Jul. 1999). A candidate target gene derived from a pathogen might, for example, cause immunosuppression of the host or be involved in replication of the pathogen, transmission of the pathogen, or maintenance of the infection.

The method of the invention can also be used to regulate the expression of an exogenous gene or "transgene" that has been introduced into a host plant or animal. For example, a transgene that is present in the genome of a cell as a result of genomic integration of the viral delivery construct can be regulated using dsRNA according to the invention.

The present invention allows the creation of plants with reduced susceptibility to climatic injury, insect damage, infection by a pathogen, or with altered fruit ripening characteristics. In these applications, the targeted gene may be an enzyme, a plant structural protein, a gene involved in pathogenesis, or an enzyme that is involved in the production of a non-proteinaceous part of the plant (i.e., a carbohydrate or lipid). By inhibiting enzymes at one or more points in a metabolic pathway or genes involved in pathogenesis, the effect may be enhanced: each activity will be affected and the effects may be magnified by targeting multiple different components. Metabolism may also be manipulated by inhibiting feedback control in the pathway or production of unwanted metabolic byproducts.

The method of the present invention is also useful to identify and characterize gene function in an organism. In this "functional genomics" approach, dsRNA is targeted to a gene of previously unknown function, and the resultant change in phenotype is observed and, optionally, quantified. This approach is useful to identify potential targets for pharmaceutics, to promote understanding normal and pathological events associated with development, to determine signaling pathways responsible for postnatal development and aging, and the like. For example, dsRNA can be designed to target a partial sequence of an expressed sequence tag (EST). Functional alterations in growth, development, metabolism, disease resistance, or other biological processes would be indicative of the normal role of the ESTs gene product. As another example, dsRNA targeted to new genes found by genomic sequencing programs or other "data mining" of genomic data can be used to understand the physiological roles of these new genes. The ease with which dsRNA can be introduced into an intact cell or organism containing the target gene allows the present invention to be used in high throughput screening (HTS) applications. For example, dsRNA can be produced by an amplification reaction using primers flanking the inserts of any cDNA or genomic DNA gene library derived from the target cell or organism.

The present invention may be useful in the study of essential genes. Such genes may be required for cell or organism viability at only particular stages of development or cellular compartments. The functional equivalent of conditional mutations may be produced by inhibiting activity of the target gene when or where it is not required for viability. The invention allows addition of RNA at specific times of development and locations in the organism without introducing permanent mutations into the target genome.

Likewise, if alternative splicing produced a family of transcripts that were distinguished by usage of characteristic exons, the present invention can target inhibition through the appropriate exons to specifically inhibit or to distinguish among the functions of family members. For example, a hormone that contained an alternatively spliced transmembrane domain may be expressed in both membrane bound and secreted forms. Instead of isolating a nonsense mutation that terminates translation before the transmembrane domain, the functional consequences of having only secreted hormone can be determined according to the invention by targeting the exon containing the transmembrane domain and thereby inhibiting expression of membrane-bound hormone.

The present invention may be used alone or as a component of a kit having at least one of the reagents necessary to carry out the in vitro or in vivo introduction of RNA to test samples or subjects, Preferred components are the dsRNA and a vehicle that promotes introduction of the dsRNA. Such a kit may also include instructions to allow a user of the kit to practice the invention.

Model Systems

Zebrafish. Successful large-scale chemical mutagenesis screens in the zebrafish have led to speculation that this organism will become the vertebrate equivalent of *Drosophila* for the study of developmental genetics (C. Nusslein-Volhard, *Science* 266, 572-574 (1994)). In order for this goal to be realized, as the zebrafish genome is further elucidated, it is imperative to develop techniques for targeted gene knockouts to make maximal use of this vertebrate system. As a vertebrate model, zebrafish has advantages over the mouse including rapid ex-utero development of the relatively transparent embryos, allowing easy access to and visualization of developmental processes. Until now, however, only one technique has been available for targeted interference with gene expression in the zebrafish. This technique employs a ribozyme to mediate a gene "knockdown" (Y. Xie et al., *Proc. Natl. Acad. Sci. U.S.A.,* 94, 13777-13781 (1997)).

Murine NIH/3T3 cells. Murine NIH/3T3 cells are an extremely well-characterized tumor cell line from mice fibroblasts, and have been used to develop and test numerous therapies, including gene therapies, intended for use in humans.

EXAMPLES

The present invention is illustrated by the following examples. It is to be understood that the particular examples, materials, amounts, and procedures are to be interpreted broadly in accordance with the scope and spirit of the invention as set forth herein.

Example I

Double-Stranded RNA Injection Blocks Gene Expression in Zebrafish

To determine whether double-stranded RNA can attenuate endogenous gene expression, single cell zebrafish embryos were injected with double-stranded RNA specifically targeted to three genes of particular interest GFP, Zf-T and Pax6.1. The phenotypic role played by GFP has been well-characterized in zebrafish; Zf-T is a reporter gene that has been very useful for dissecting promoter activity in zebrafish embryos; and Pax6.1 is a gene that has been thoroughly studied in other organisms.

Materials

The GFP expression vector, pEGFP-N1 (GenBank accession number U55762.1), was obtained from Clontech, Inc.

Isolation of Zebrafish RNA

Figure 1B:
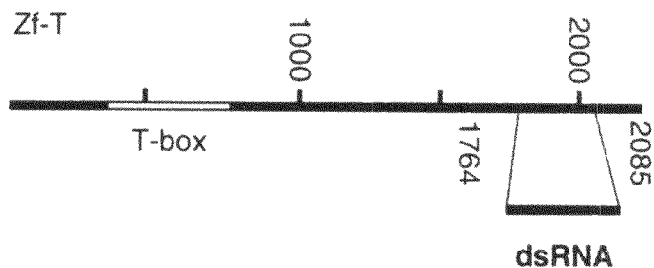
Figure 1C:
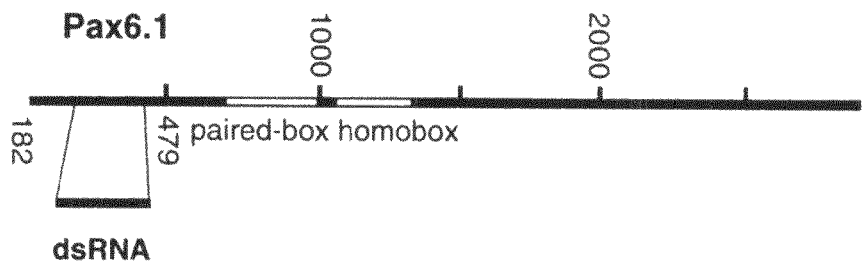

RNA from staged zebrafish embryos was obtained using the ULTRASPEC RNA isolation kit (Biotecx Laboratories, Inc.). Fifty embryos are sufficient to obtain the necessary amount of RNA Generation of Double-Stranded RNA Zf-T cDNA fragment. A 321 bp Zf-T cDNA fragment (nucleotide number 1764 to 2085; GenBank accession number S57147) was generated by reverse transcriptase-polymerase chain reaction (RT-PCR) from RNA of 8 hour zebrafish embryos. The sequence of upstream primer was 5' TTGGAACAACTTGAGGGTGA 3' (SEQ ID NO:1) and the downstream primer was 5'CGGTCACTTTTCAAAGCG-TAT 3' (SEQ ID NO:2). To avoid targeting related genes, the primers were designed to amplify a unique portion of the gene that lies outside of the T-box region (FIG. 1).

Ntl insertion sequence cDNA fragment. A 488 bp cDNA fragment of the ntl insertion sequence (GenBank accession number X71596) was also generated by RT-PCR. This fragment disrupts Zf-T in a ntl mutant allele and served as a negative control for the double-stranded Zf-T RNA injection. The sequence of the upstream primer was 5' ACCCTATA-CACCCCCACCTC 3' (SEQ ID NO:3) and the downstream primer was 5' ATAATAGGCACCGCTCATGC 3' (SEQ ID NO:4).

Pax 6.1 cDNA fragment. A 298 bp Pax6.1 cDNA fragment (GenBank accession number X63183) was generated by RT-PCR of RNA obtained from 24 hour zebrafish embryos. The upstream primer was 5'TTTTCGAGGTTCCCTTGTTG (SEQ ID NO:5) and the downstream primer was 5'AGC-CTTTGTATCCTCGCTGA (SEQ ID NO:6). This cDNA fragment lies 5' to the paired box and homeobox.

Nkx cDNA fragments. cDNA fragments for zebrafish Nkx 2-3, 2-5 and 2-7 genes were obtained in a similar manner. For the Nkx 2-3 gene (GenBank accession number U66571), the upstream primer was 5' AACCGTGTTTAACGGGATCA (SEQ ID NO:7) and the downstream primer was 5' GGTTG-CACTGGCACTACCAT (SEQ ID NO:8), yielding a 291 base pair product, representing positions 775-1065 of the Nkx 2-3 coding sequence. For the Nkx 2-5 gene (GenBank accession number U66572), the upstream primer was 5' CATCTTG-CATGCTGTCCACT (SEQ ID NO:9) and the downstream primer was 5'AGATCTTCACCCGGGTCTTC (SEQ ID NO:10), yielding a 250 base pair product, representing positions 232-481 of the Nkx 2-5 coding sequence. For the Nkx 2-7 gene (GenBank accession number U66573), the upstream primer was 5' CATTTGCCAACACGAGTCAA (SEQ ID NO:11) and the downstream primer was 5' CCAGTCCAGT-GCCATTTGAT (SEQ ID NO:12), yielding a 141 base pair product, representing positions 911 to 1051 of the Nkx 2-7 coding sequence.

GFP cDNA fragment. A cDNA fragment at the 5' end off the GFP coding sequence was used as template for double-stranded GFP RNA. This 187 bp partial cDNA GFP fragment was obtained using PCR by amplifying a GFP fragment from pEGFP-N1 using chimeric primers containing T7 promoter specific sequence and a GFP sequence. The forward primer was 5'-TAATACGACTCACTATAGGGTAAACGGC-CACAAGTTC (SEQ ID NO:13) and the reverse primer was 5' -TAATACGACTCACTATAGGGTCGTGCT-GCTTCATGTG (SEQ ID NO:14), yielding a 187 base pair product representing positions 743 to 930. T7 polymerase was used to simultaneously generate sense and antisense strands using this PCR-generated fragment as a template.

Figure 2:
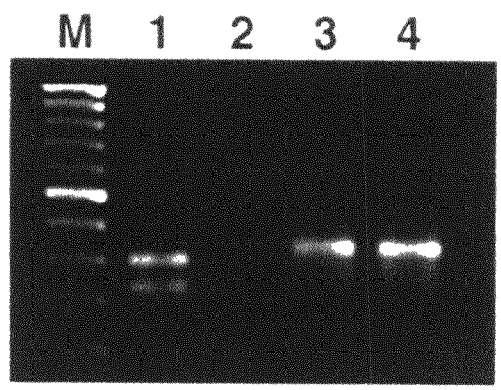
FIG. 2 is an agarose gel that demonstrates annealing of double-stranded Zf-T RNA. Sense and antisense Zf-T RNA strands (lane 1) were treated with RNAse A before (lane 2) and after (lane 4) annealing. Each lane was loaded with 0.5 μg of treated (lanes 2 and 4) or untreated RNA (lane 1 and 3).

Generation of double-stranded RNA. The Zf-T, Pax6.1, GFP, and Nkx 2-3, 2-5 and 2-7 fragments thus obtained were each individually cloned into pGEM-T vectors containing T7 and SP6 promoters (Promega, Madison, Wis.). The clones were sequenced to ensure their identity. Double-stranded RNA was then generated from these cloned sequences. To produce the double-stranded RNA, two sets of PCR products were first generated from the cloned fragment (FIG. 1). One PCR product was generated using a primer that is antisense to the T7 promoter sequence, and the other PCR product was generated using a primer that was antisense to the SP6 promoter. The other primers used in these PCRs were specific to the 3' end of the inserted gene fragment relative to the promoter-specific primer being used. PCR products were purified on CENTRICON-100 columns according to manufacturer's instructions (Centricon). T7 RNA polymerase or SP6 RNA polymerase was used to synthesize RNA from each of these templates. In vitro transcription reactions were incubated at 37° C. for two hours. At completion of each RNA polymerase reaction, RNAse-free DNAse (e.g., RQ Dnase) was added to the reaction to remove the DNA template. The reaction was incubated at 37° C. for an additional 15 minutes, then at 70° C. for 10 minutes to inactivate the DNAse. RNA was generated in this manner in order to avoid the small amounts of contaminating RNA that can be generated from the opposite strand in RNA synthesis reactions in which plasmids are used as templates. This is especially important for the control experiments since very small amounts of dsRNA can silence gene expression. RNA was purified by centrifugation through a QUICKSPIN column (Boeringer Mannheim); a Sephadex G25 or G50 size exclusion column can also be used. The double-stranded RNA was formed by mixing equal quantities (i.e., 1:1 molar ratios) of the single-strand RNAs that had been denatured at 70° C. for 5 minutes in 80 mM KCl and incubating 1-2 hours at 37° C. Prior to injection, the efficiency of RNA annealing was determined by RNAse A (0.5 µg/ml) digestion for 15 minutes at 37° C. (FIG. 2).

Microinjection of Single Cell Zebrafish Embryos

Individual single cell embryos were placed in fish embryo water on agarose ramps in petri dishes. Micropipettes are pulled to a fine point and the tip of the pipette is broken using fine tip forceps. The double-stranded RNA is loaded into the micropipette by suction and injected just above the yolk under a dissecting microscope. Single cell embryos are injected with approximately $10^6$ molecules of dsRNA. The injected embryos were subsequently incubated in embryo medium (Westerfield, 1993) at 28.5° C. for 12 hours to 5 days.

RT-PCR

Reverse transcriptase-polymerase chain reaction (RT-PCR) was used to quantify the message level after double-stranded RNA treatment. One hundred zebrafish embryos injected with double-stranded RNA targeted to Zf-T, control double-stranded RNA or uninjected controls were collected at 10 hours. RNA was extracted by RNAEasy mini column (Qiagen). RNA samples were treated with 1 unit RNAse free-DNAse I/1 µg RNA, at 37° C. for 15 minutes. The RNA was extracted with phenol/chloroform and precipitated with 2.5 volumes of 95% ethanol and 50 ng RNA was used for PCR to confirm that there was no DNA contamination. RNA (0.1 µg) was combined with 50 ng of oligo(dT)$_{15}$ primers in 10 µl water at 65° C. for 10 minutes then cooled to room temperature for 5 minutes. The reverse transcription was carried out at 42° C. for 1.5 hours with 0.1 µg of total RNA, 0.1 µg of random primer, 20 units RNasin, 200 µM dNTPs, 200 U Superscript II RNAse H reverse transcriptase (GIBCO BRL Inc.), 75 mM KCl, 3 mM MgCl$_2$, 20 mM DTT in 50 mM Tris-HCl pH 8.3, at a final volume of 20 µl. One unit of ribonuclease H was added to digest the RNA at 37° C. for 30 minutes. The reaction was stopped by heating at 94° C. for 5 minutes.

The PCR was performed in 50 µl containing 2 µl cDNA product from the reverse transcription, 200 µM dNTPs, 10 pmol primers, and 1.0 unit of Taq polymerase, 50 mM KCl, 1.5 mM MgCl$_2$, and 0.001% gelatin in 10 mM Tris-HCl, pH 8.3. A GenAmp PCR System 2400 (Perkin Elmer) was used with the following program: 94° C., 1 minutes, 29 cycles of: 94° C. for 25 seconds; 56° C. for 20 seconds; 72° C. for 30 seconds; final extension was at 72° C. for 7 minutes. The PCR product was separated on a 2% agarose gel. The PCR product of the Zf-T gene (GenBank accession number S57147) is 271 bp. It covers the cDNA region of Zf-T from base 1381 to 1750. The forward primer sequence was 5' TTGATCTTG-GCTTCAGGAGG 3' (SEQ ID NO:15) and downstream primer was 5' TGCAATGGTTACCAGTTTTGA 3' (SEQ ID NO:16). Primers for zebrafish β actin (used as a control) (GenBank accession number AF 025305) were upstream primer 5' CCCTTGACTTTGAGCAGGAG 3' (SEQ ID NO:17) (starting from base 665) and downstream primer 5' ACAGGTCCTTACGGATGTCG 3' (ending at base 886) (SEQ ID NO:18). The PCR product size was 221 bp.

In Situ Hybridizations and Histology

In situ hybridizations were performed as previously described (Wilkinson, 1992). Sense and antisense probes were generated from a region of the Zf-T gene lying outside the region targeted by the double-stranded RNA. Embryos were fixed in 4% paraformaldehyde at 4° C. or Bouin's fixative at room temperature. For histology, embryos were dehydrated in an alcohol series then cleared in xylene. Embryos were embedded in paraffin and sectioned on a microtome at a thickness of 5 µm and were mounted. The slides were deparaffinized, rehydrated and placed in acid alcohol (1% HCl in 70% ethanol) for 5 min, then rinsed in distilled water. Giemsa staining was performed as previously described (Vacca, 1985).

Results

Targeted Double-Stranded RNA Blocks Transient Expression of GFP

Figure 3:
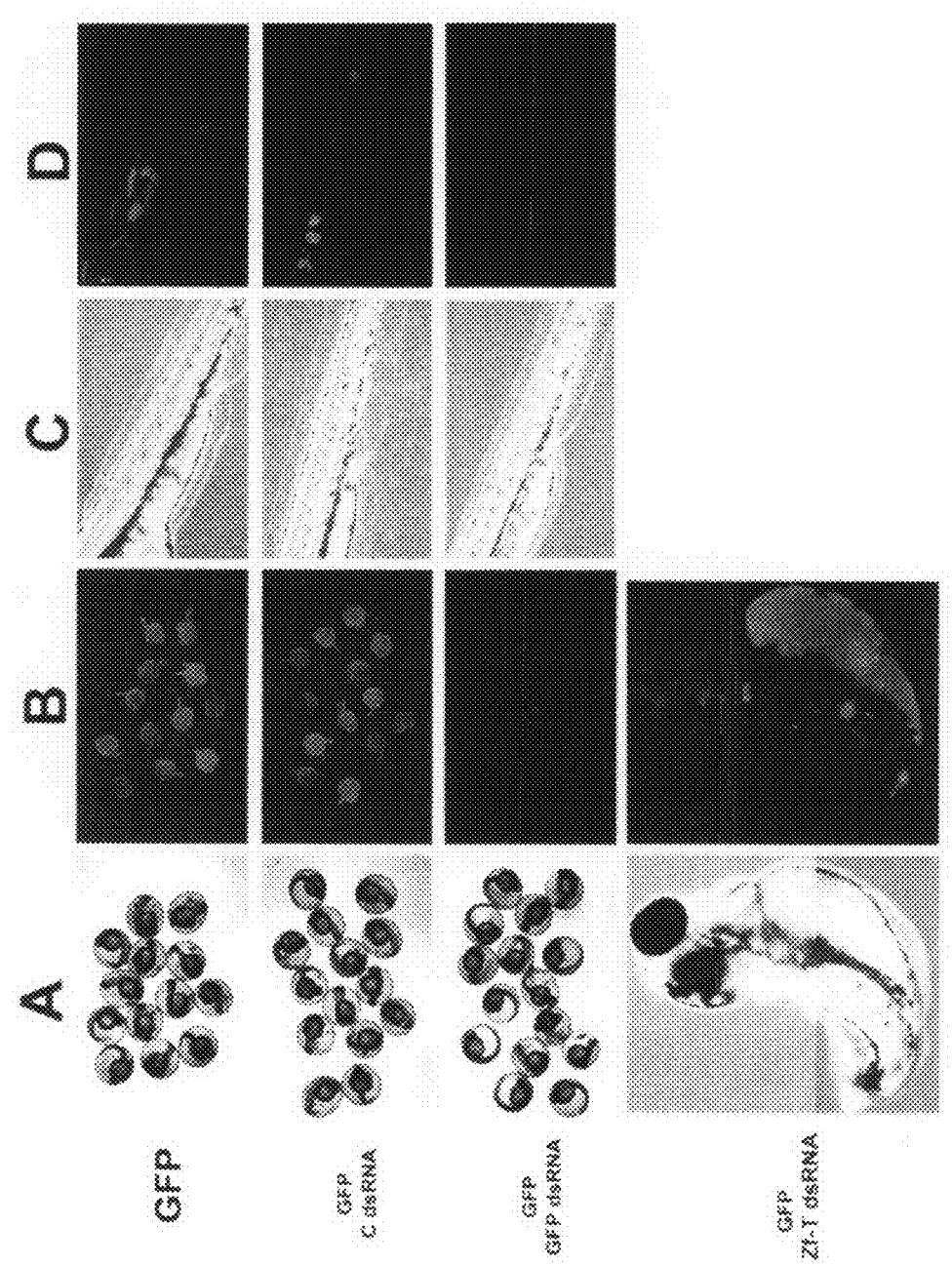
FIG. 3 shows the effect of GFP double-stranded RNA injection on the transient expression of GFP in zebrafish embryos. Columns A and C show the same field of embryos by light microscopy as seen under fluorescence in columns B and D, respectively. Columns A and B show embryos injected at the single cell stage while columns C and D show embryos injected at the 16-cell stage. Rows 1-3 are designated by treatment to the left as injected with the GFP expression vector alone (row 1), GFP expression vector with control double-stranded RNA (row 2), or GFP expression vector with GFP double-stranded RNA (row 3). The embryo shown in row 4 was injected at the single cell stage with GFP and Zf-T double-stranded RNA. While the zebrafish yolk does show some autofluorescence at higher magnifications, it is not apparent at the magnification shown in columns A and B. The yolk fluorescence seen here is from the GFP expression vector and is specifically attenuated by double-stranded RNA to GFP. On the other hand double-stranded RNA targeted to Zf-T does not interfere with GFP expression and since this embryo shows the ntl phenotype, the presence of the GFP expression vector does not attenuate the function of the Zf-T double-stranded RNA.

FIG. 3 shows the effect of double-stranded GFP RNA injection on transient GFP expression in zebrafish single cell or 16-cell zebrafish embryos. Microinjection of the GFP expression vector pEGFP-N1 into single cell zebrafish embryos resulted in the transient expression of GFP in 85% of the embryos. GFP expression was monitored by fluorescence microscopy throughout early embryogenesis. GFP-targeted double-stranded RNA was generated for the region shown in FIG. 1, and embryos were co-injected with either GFP double-stranded RNA or a control double-stranded RNA (i.e., the ntl insertion sequence dsRNA). When embryos were co-injected with pEGFP-N1 and $2.9 \times 10^5$ double-stranded RNA molecules, fewer than 3% of embryos had detectable GFP expression. Eighty-four percent (84%) of embryos co-injected with control double-stranded RNA showed abundant GFP expression.

When the embryos were injected at the 16-cell stage, injection of pEGFP-N1 alone or pEGFP-N1 with control double-stranded RNA resulted in embryos with scattered, brightly fluorescent cells at 36 hours of development Co-injection of GFP double-stranded RNA with the pEGFP-N1 completely quenched the GFP signal.

When Zf-T double-stranded RNA was co-injected with the pEGFP-N1 plasmid into single cell embryos, the embryos had the ntl phenotype described below, and showed brilliant GFP expression in scattered cells. These results show that expression of a transiently transfected plasmid can be specifically attenuated by targeted double-stranded RNA.

Targeted Double-Stranded RNA Blocks Zf-T Gene Expression

The T gene has dramatic phenotypes in mutant and transgenic animals. The mouse T (Brachyury) gene is required for normal mesoderm development and extension of the body axis (Herrmann et al., 1990). The zebrafish homologue of the T gene (Zf-T) plays an important role in midline development. Mutation of the Zf-T gene is known to result in the no tail (ntl) mutant phenotype, a Brachyury orthologue. The ntl embryos closely resemble mouse T/T mutant embryos in that they lack a differentiated notochord and show poor development of the caudal body (M. Halpern et al., Cell 75, 99-111 (1993)).

Brachyury encodes a member of the T-box transcription factor family that is expressed in the notochord and is essential for the proper development of midline structures. Loss of function of this gene causes arrested development of notochord. The lack of notochord differentiation leads to disrupted morphogenesis of the mesoderm during gastrulation. This is particularly evident in the appearance of the somites, which lack the chevron-shaped organization found in wild-type embryos.

Figure 4:
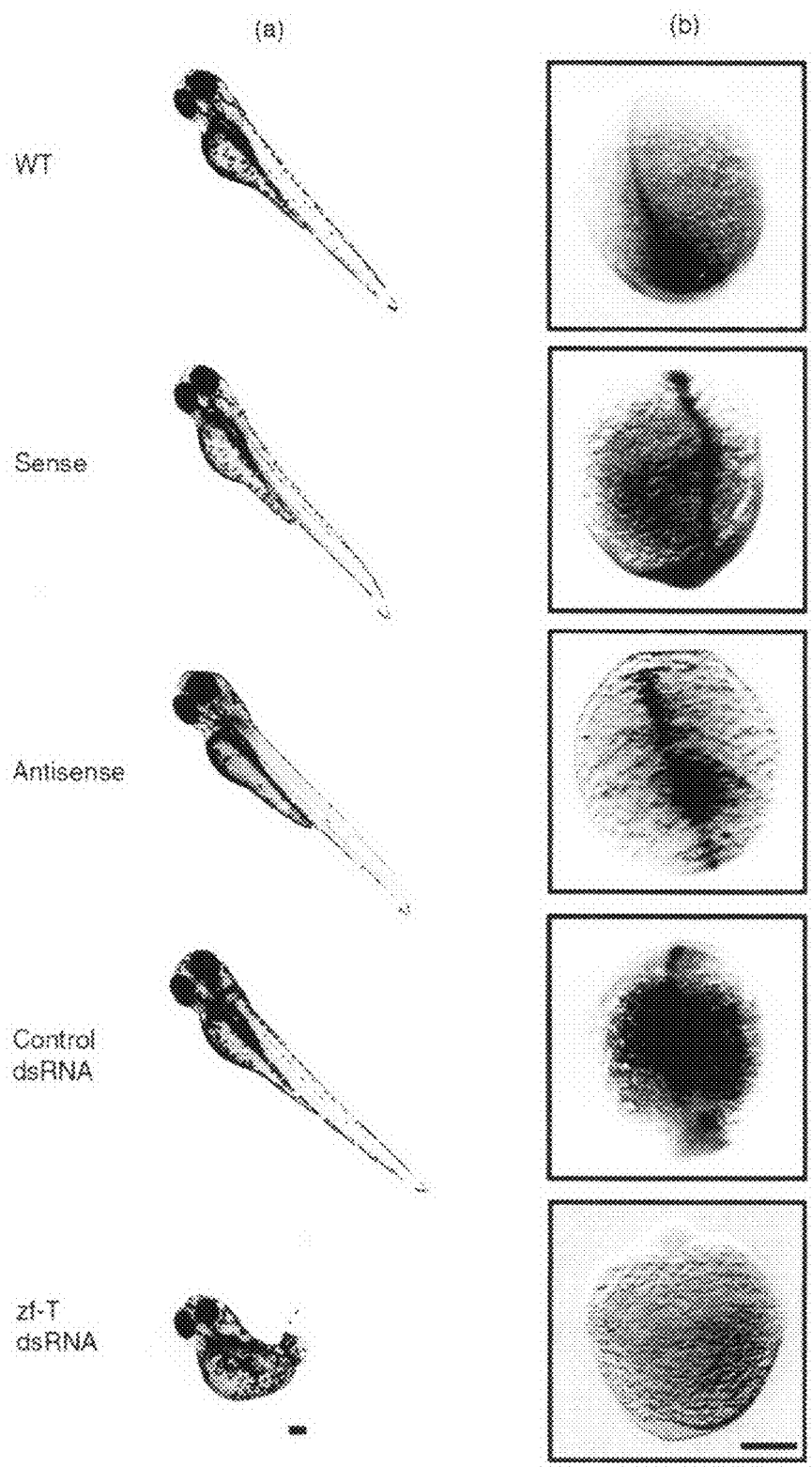
FIG. 4 shows the ntl phenocopy produced by microinjection of double-stranded Zf-T RNA into single cell embryos. As shown in Column A, no abnormal phenotypes were apparent subsequent to injection of Zf-T sense or antisense RNA. The injection of double-stranded control RNA also produced no apparent phenotypes. Embryos injected with double-stranded Zf-T RNA exhibited greatly reduced tails and their somites lacked the typical chevron shape of those in the wild type embryos. The embryos shown are 5 days old. As shown in Column B, in situ hybridizations demonstrate that 9 hour embryos lack Zf-T expression following double-stranded Zf-T RNA injection into single cell embryos, although sense RNA, antisense RNA, and double-stranded control RNA injection had little effect on Zf-T expression. Scale bars=100 μm.

FIG. 4 shows the effect of double-stranded Zf-T RNA injection on Zf-T expression in zebrafish single cell embryos. We found 71% of the zebrafish embryos that had been injected at the single cell stage with approximately $10^4$ double-stranded RNA molecules generated from the Zf-T cDNA fragment had phenotypes that were grossly similar to that of the ntl mutant, i.e., truncated tails and disorganized somites (FIG. 4a). Injection of Zf-T single-stranded sense or antisense RNA, or double-stranded RNA generated from the control ntl inserted sequence, did not lead to a significant incidence of this phenotype (Table 1). Simultaneous injection of sense and antisense RNA that were not annealed did not result in a significant incidence of the ntl phenotype.

After injection of the Zf-T double-stranded RNA, the Zf-T message was undetectable by in situ hybridization in 20% of the embryos (11/56) and weakly expressed in another 50% of embryos injected with Zf-T double-stranded RNA (FIG. 4b). Semi-quantitative RT-PCR using β actin to control for PCR efficiency and loading, showed an overall 75% reduction in the Zf-T message level from that seen in embryos injected with an unrelated double-stranded RNA.

To determine whether the Zf-T double-stranded RNA had a global effect on gene expression, we co-injected it with pEGFP-N1 into single cell embryos (FIG. 3, row 4). In these experiments, every embryo that exhibited a ntl phenotype also had significant GFP expression. This supports the view that the phenotypes generated by the injection of double-stranded RNA are not the result of non-specific effects on gene expression.

Phenocopy of ntl Generated by Infection of Zf-T Double-Stranded RNA

Figures 5, 6:
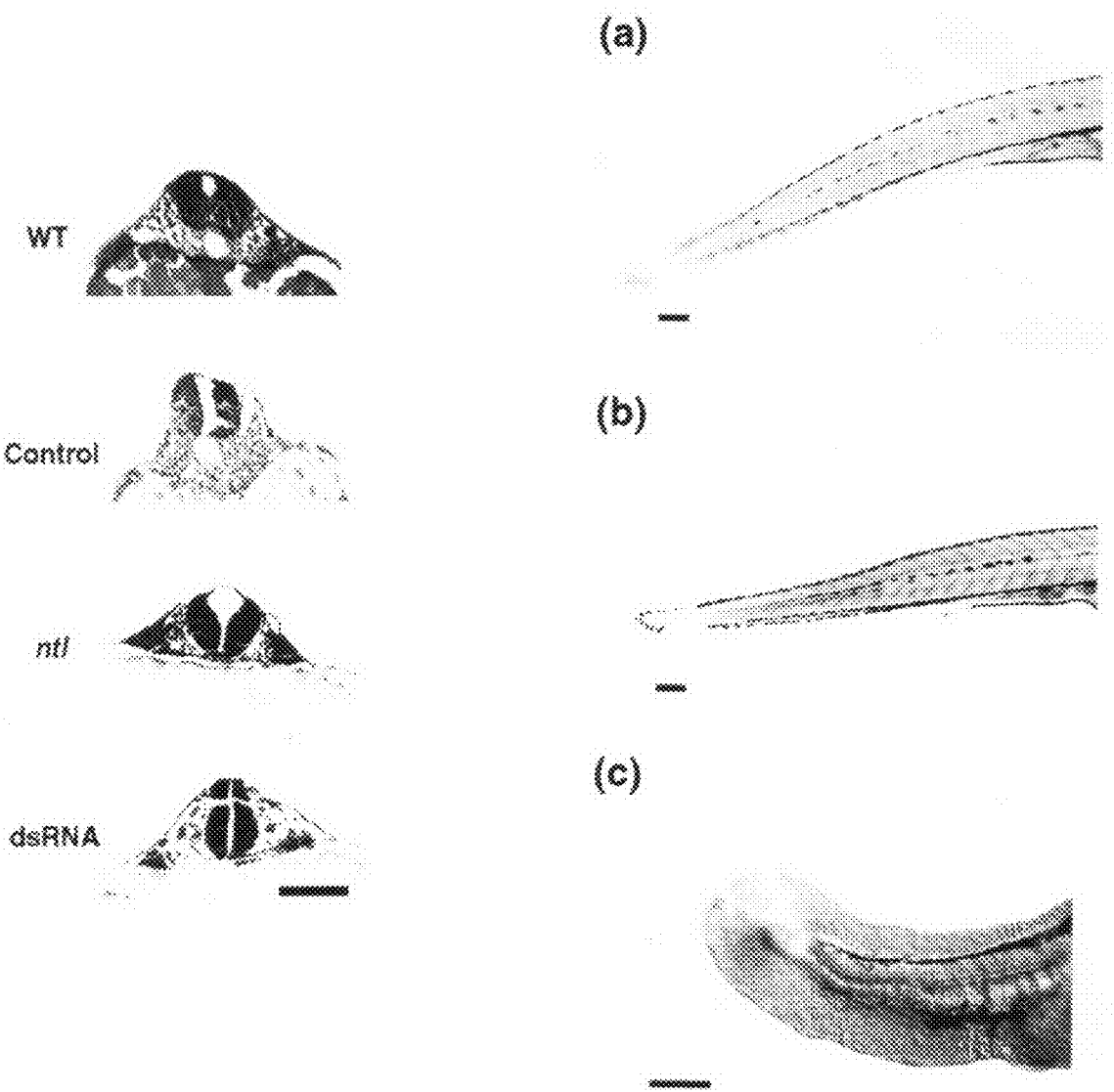
FIG. 5 shows the effect of Zf-T double-stranded RNA injection on development of the notochord in 24 hour zebrafish embryos. Wildtype zebrafish and embryos injected with the control double-stranded RNA developed an obvious notochord. Ntl mutant embryos lacked a notochord along the entire body axis. Twenty-one percent of the embryos injected with the Zf-T double-stranded RNA also lacked a notochord along the entire body axis. Another 60% lacked notochord in the posterior portion of the body axis. Scale bars=100 μm.
FIG. 6 shows the effect of Zf-T double-stranded RNA injection on development of the somites in zebrafish embryos. Both (a) wild type zebrafish embryos and (b) those injected with control double-stranded RNA developed characteristic chevron-shaped somites, whereas (c) zebrafish embryos that had been injected with double-stranded Zf-T RNA developed somites that lacked the typical chevron shape. Scale bars=100 μm.

To determine whether the mutant zebrafish generated by injection of Zf-T double-stranded RNA into single cell embryos phenocopied the ntl mutant, cross-sections of 24 hour embryos injected with Zf-T double-stranded RNA or control double-stranded RNA were examined. The results are shown in FIG. 5. Embryos injected with the Zf-T double-stranded RNA generally lacked a fully developed notochord as is seen in naturally occurring mutants, while those injected with the control double-stranded RNA had a notochord similar to that seen in uninjected embryos. Twenty-one percent of the embryos examined that had been injected with Zf-T double-stranded RNA completely lacked notochord (6/28). Somites in the Zf-T attenuated embryos were disrupted in a similar fashion to that seen in ntl zebrafish (FIG. 6). The typical chevron appearance of the somites was lacking, but somites were not fused across the midline as is seen in floating head mutants.

Figure 7:
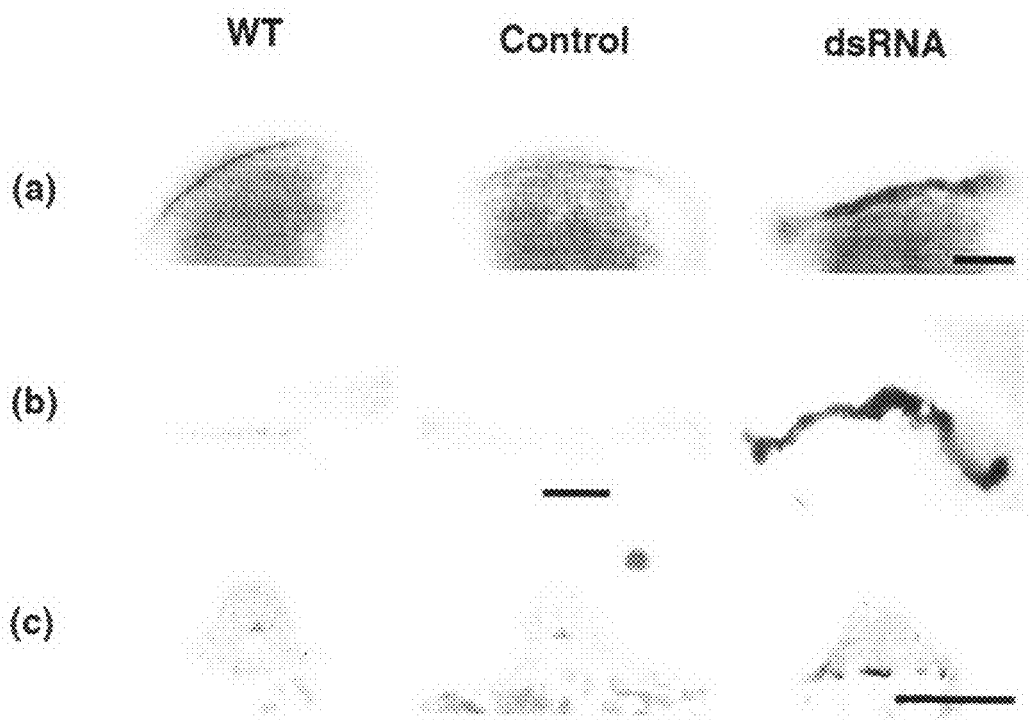
FIG. 7 shows the effect of Zf-T double-stranded RNA injection on the expression of sonic hedgehog. RNA in situ hybridizations for shh show a one-cell-wide row of cells in the floorplate that are labeled along the length of the trunk and tail in wild type embryos and embryos injected with a control double-stranded RNA; (a) is a top view; (b) is a side view; and (c) is a cross-section. In embryos injected with Zf-T double-stranded RNA, the floorplate has expanded and expression of shh is 3-4 cells wide, similar to the expression found in the ntl mutant. Scale bars=100 μm.

Effect of Zf-T Double-Stranded RNA on the Expression of Sonic Hedgehog and Floating Head The expression patterns of shh and flh, two genes that are also essential to proper midline development in zebrafish, were examined by in situ hybridization. FIG. 7 shows the effect of Zf-T double-stranded RNA injection on the expression of shh. In 27% of the embryos examined (15/26), the expression pattern of shh throughout the floorplate of the embryos injected with the Zf-T double-stranded RNA was 3-4 cells wide. This is identical to the expression pattern found for this gene in ntl embryos (Halpern et al., 1997). More than 50% of the embryos examined had a similar, but less complete alteration of shh expression. In the embryos injected with the control double-stranded RNA, in situ hybridization showed shh expression limited to a one-cell stripe along the midline as is found in wild-type embryos.

Figure 8:
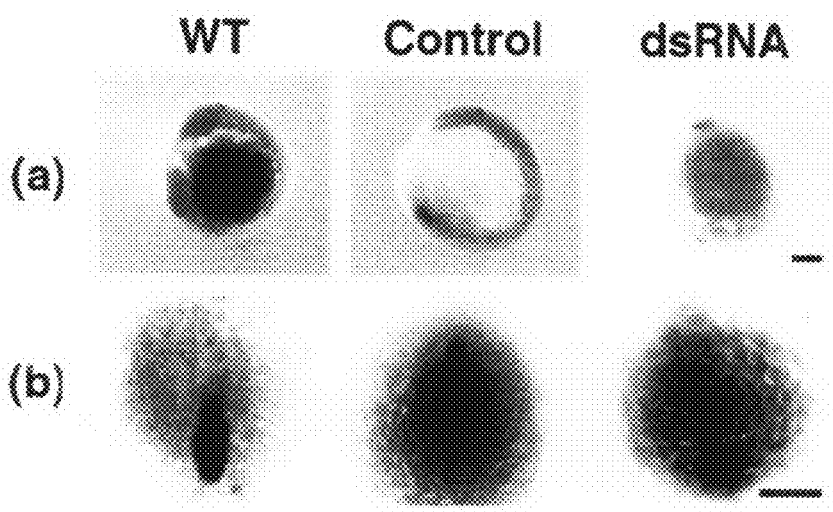
FIG. 8 shows the effect of Zf-T double-stranded RNA injection on the expression of floating head: (a) side views and (b) dorsal views of tailbud stage zebrafish embryos. RNA in situ hybridizations show that flh is expressed in an axial stripe in the wild type embryos and in those injected with the control double-stranded RNA. An embryo injected with Zf-T double-stranded RNA shows diffuse flh expression in the tailbud and intense expression in the anterior nervous system, while expression in the body axis was greatly diminished. Scale bars=100 μm.

In wild-type zebrafish embryos, flh is expressed in the anterior and posterior nervous system and in a narrow axial strip. The effect of Zf-T double-stranded RNA injection on the expression of flh is shown in FIG. 8. In 33% of the embryos examined (6/18), expression of flh in the Zf-T double-stranded RNA injected embryos was unaffected in the anterior and posterior nervous system but was greatly diminished or absent along the axis. Embryos injected with Zf-T double-stranded RNA also show diffuse and broadened flh expression in the tailbud. This is similar to the expression pattern of flh found in the ntl mutant (A. Melby et al., Dev.

Dyn. 209, 156-165 (1997)). This partial effect on flh expression was observed in more than 80% of the embryos examined.

Dose-Response for Generation of the ntl Phenotype

Figure 9:
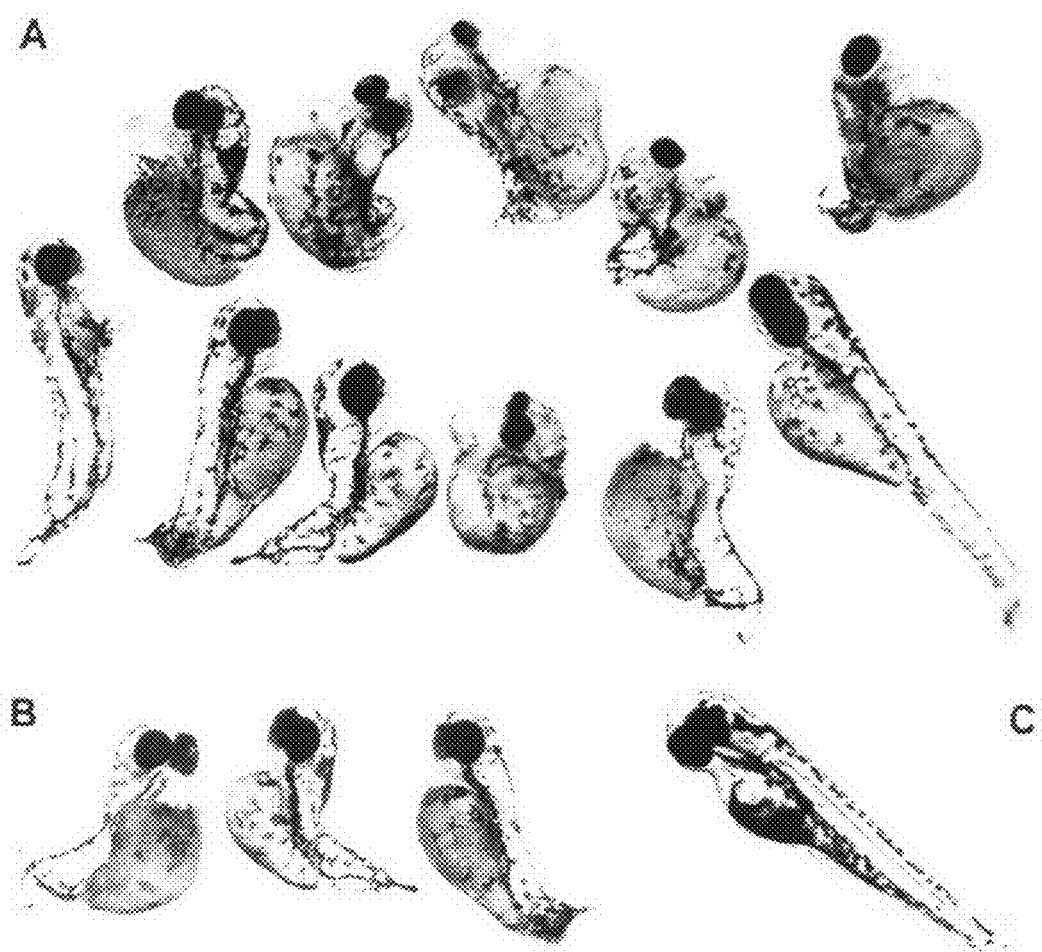
FIG. 9 shows (a) the range of phenotypes observed in 72 hour zebrafish embryos following injection of Zf-T double-stranded RNA; (b) 3 embryos with a complete phenotype; histological sections were used to confirm that the notochord was absent; and (c) one embryo with a partial phenotype which was confirmed by histological section to have an anterior notochord.

To determine the number of double-stranded RNA molecules required to generate a phenotype, single cell embryos were injected with approximately 1 ntl of a solution containing double-stranded Zf-T RNA concentrations ranging from $1.6 \times 10^5$ to $5.0 \times 10^8$ molecules of double-stranded RNA/nl. Phenotype was determined for each embryo at 48 hours post-injection. As can be seen in Table 1, embryos that had been injected with $10^6$ or more Zf-T double-stranded RNAs exhibited a very high incidence of the ntl phenotype. A grossly complete phenotype was observed in more than 20% and a partial phenotype was observed in 50% of these embryos (Table 1; FIG. 9). Embryos injected with $4.0 \times 10^6$ double-stranded RNAs or less did not show a significant incidence of the ntl phenotype. Embryos injected with a control double-stranded RNA were phenotypically normal. Embryos injected simultaneously with sense and antisense single-stranded RNAs also did not display abnormal phenotypes.

TABLE 1

The injected RNA molecular numbers and embryos with phenotypic changes.

| Injection | Molecules(1) ($\times 10^6$) | Number of embryos | Viable embryos | Phenotypic change | | |
|---|---|---|---|---|---|---|
| | | | | None | Partial | Full |
| Uninjected | 0 | 296 | 239 | 239 | 0 | 0 |
| S ssRNA(2) | 100 | 768 | 621 | 619 | 2(0.6%) | 0 |
| A ssRNA(3) | 100 | 715 | 583 | 580 | 3(0.5%) | 0 |
| S/A ssRNA(3) | 100 | 708 | 587 | 585 | 2(03%) | 0 |
| C dsRNA(4) | 100 | 959 | 815 | 810 | 5(0.6%) | 0 |
| Zf-T dsRNA | 0.16 | 550 | 468 | 466 | 2(0.4%) | 0 |
| | 0.8 | ND | 79 | 73 | 4(5%) | 2(3%) |
| | 4 | 328 | 288 | 275 | 11(4%) | 2(0.7%) |
| | 20 | 257 | 229 | 196 | 23(10%) | 10(4%) |
| | 50 | 161 | 129 | 79 | 38(29%) | 12(9%) |
| | 100 | 1975 | 1618 | 455 | 839(51%) | 322(20%) |
| | 290 | 769 | 531 | 93 | 275(51%) | 163(31%) |
| | 500 | 1206 | 822 | 97 | 438(53%) | 287(35%) |

(1)The injected RNA numbers for each embryo.
(2)Single-stranded RNA of sense (S) and antisense (A) direction.
(3)S/A indicates the unannealed sense and antisense RNA mixture.
(4)Control (C) double-stranded RNA.

Thus, microinjection of double-stranded Zf-T RNA resulted in a high incidence of a phenotype similar to that of ntl. Furthermore, Zf-T gene expression could not be detected by in situ hybridization and the message was decreased by 75% as monitored using semiquantitative RT-PCR in 12 hour embryos that had been injected with the double-stranded RNA. Expression of the zebrafish genes sonic hedgehog and floating head were altered in the embryos microinjected with the Zf-T double-stranded RNA in a manner that is remarkably similar to the zebrafish no-tail mutant.

Targeted Double-Stranded RNA Blocks Zf-Pax6.1 Gene Expression

Another unique and dramatic phenotype is associated with a naturally occurring Pax6 mutation, which was found in the mouse mutant small eyes. These embryos lack the lens placodes and normal forebrain structures. Zebrafish Pax6.1 transcripts can first be detected in the presumptive forebrain and hindbrain regions of the neural plate. Expression has also been observed in the optic vesicles and lens placodes, confirming that the Pax6.1 protein is expressed in those areas of the eye where it is assumed to control differentiation. These expression patterns correlate well with a role for Pax6.1 in lens placode and brain development in zebrafish. A second closely related gene, Zf-Pax6.2, has an expression pattern that overlaps with that of Pax6.1 in zebrafish embryos.

Figure 10:
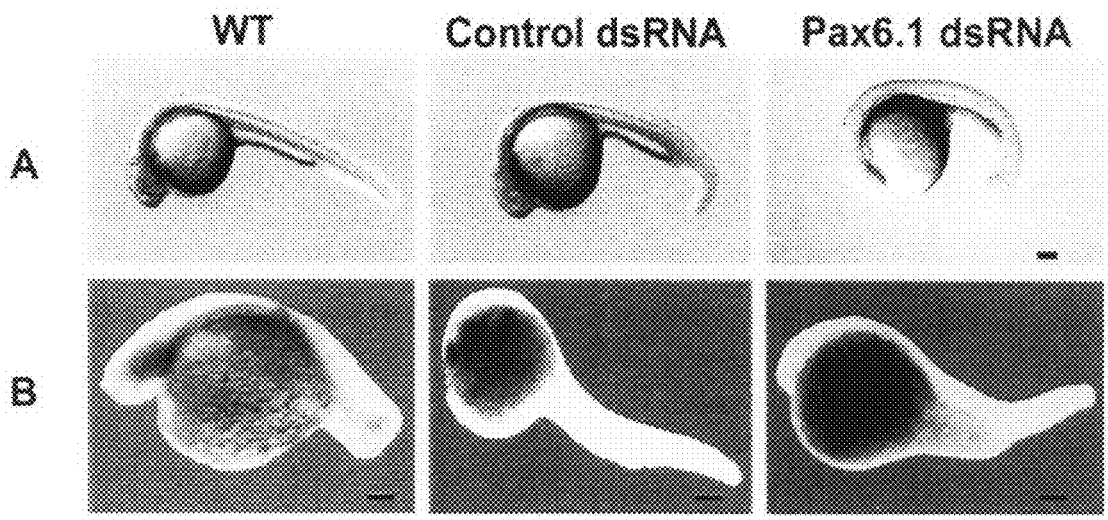
FIG. 10 shows that the absence of Pax6.1 expression results in severe abnormalities of head development; (a) 48 hour embryos injected with double-stranded control RNA had normal phenotypes. Microinjection of double-stranded Zf-Pax6.1 RNA into single cell zebrafish embryos resulted in 25% of the embryos having reduced eyes often accompanied by diminished and disorganized forebrains; (b) in situ hybridizations demonstrated that 24 hour embryos lack Zf-Pax6.1 expression following double-stranded Zf-Pax6.1 RNA injection into single cell embryos, although double-stranded control RNA injection had no apparent effect on Zf-pax6.1 expression. Scale bars=100 μm.

As shown in FIG. 10, injection of double-stranded RNA of the zebrafish Pax6.1 cDNA fragment resulted in embryos with grossly underdeveloped heads and absent or greatly diminished eyes. Expression of Pax6.1 message was absent in embryos injected with double-stranded RNA, but undiminished in embryos injected with ntl double-stranded RNA. Twenty-five percent of the embryos injected with the Zf-Pax6.1 double-stranded RNA exhibited phenotypes. Thus, microinjection of double-stranded RNA targeted to Pax6.1 was associated with depressed expression of Pax6.1 and resulted in absent or greatly reduced eye and forebrain development, similar to the phenotype seen in mouse mutants.

Targeted Double-Stranded RNA Blocks Zf-Nkx 2-7 Gene Expression

Nkx2-5 was identified by virtue of its homology to the Drosophila gene tinman. Null expression of tinman is associated with absent development of the Drosophila dorsal vessel, which is similar in some ways to the vertebrate heart. A number of members of the Nkx gene family play crucial roles in normal vertebrate heart development. Several Nkx family members are expressed in the developing heart of one or more vertebrate species, including Nkx 2-3, 2-5, 2-6, 2-7, and 2-8. Hemizygous mutations in the human Nkx 2-5 gene, for example, are located on chromosome 5q34, are associated with defective cardiac septation and congenital heart block. Three Nkx family members known to be expressed in the zebrafish heart field: Nkx 2-3, Nkx 2-5, and Nkx 2-7.

In this experiment, embryos that were injected with Zf-Nkx 2-7 double-stranded RNA exhibit altered heart morphology and the hearts function poorly.

Targeted Silencing of Multiple Genes

Figure 11:
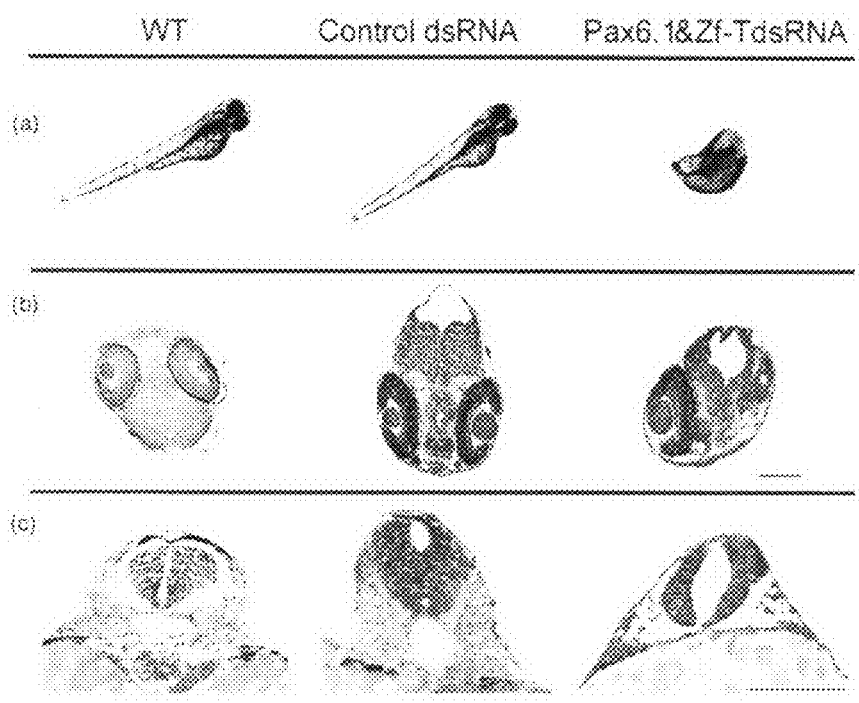
FIG. 11 shows that co-injection of the Zf-T and Zf-Pax6.1 double-stranded RNA. generates embryos with defective notochords and eyes; (a) at 5 days old, zebrafish embryos show significant defects in the eyes and tail; (b) cross sections of 48 hour embryos show that these defects included diminished eye and brain structures and (c) diminished or lacking notochord along with disorganized somites in the tail. Scale bars=100 μm.

As shown in FIG. 11, embryos that were injected simultaneously with Zf-T and Zf-Pax6.1 double-stranded RNA exhibited defective development of both the tail and head, combining the phenotypic defects associated with mutations of either gene alone. Examination of cross-sections through the head confirmed that eye and brain structures were defective in embryos injected with Zf-T double-stranded RNA.

Cross-sections through the tail region showed that notochord was lacking or greatly diminished and somites were disorganized. There was a greater incidence of defects in the tail region (greater than 90%) than in the eye or head (25%). This demonstrates that multiple genes can be simultaneously targeted for diminished expression by injection of targeted double-stranded RNAs.

Discussion

We have now shown that targeted gene silencing can be accomplished in a vertebrate embryo by injection of double-stranded RNA into single cell embryos. This method allowed us to disrupt the activity of specific genes encoding the zebrafish homologue of Brachyury (Zf-T), zebrafish Pax6.1 and the reporter gene, GFP. We also have shown that multiple genes can be targeted simultaneously using this method. In addition, embryos that were co-injected with a GFP expression vector and Zf-T double-stranded RNA developed ntl phenotypes while GFP expression was unaffected, showing that the effects of the Zf-T double-stranded RNA are not non-specific.

Depending on the timing and/or amount of dsRNA injected, partial phenotypes of varying severity can be generated. In cases where null phenotypes are particularly severe, this allows the identification of effects that would ordinarily be missed. That is, by permitting gene silencing at later stages of development, the technique has allowed us to explore the effects of blocking the expression of a gene whose inhibition would be lethal at an earlier developmental stage. This has allowed us to unmask potential roles for Zf-T in developmental processes in which it had not been previously implicated. The most severe phenotypes mirror those found in animal mutant models, such as the zebrafish ntl mutant, naturally occurring mutation in Zf-T, and the mouse mutant small eyes, which is deficient in Pax6 expression.

Functionally attenuating expression of Zf-T resulted in a reproducible phenotype that mirrored that found of the ntl mutant where the same gene was altered by an insertional mutation. Interestingly, we were able to use this inserted sequence as a negative control for these experiments as it produced no phenotype. By a number of criteria, more than 20% of all embryos injected with the Zf-T double-stranded RNA developed in a manner that phenocopied the ntl mutant. Zf-T gene silencing produced by injection of double-stranded RNA was apparent at the message level and by the specific phenotypes that were generated. In the zebrafish embryos, co-injection of unannealed sense and antisense RNA strands did not result in a high percentage of mutants. This is in contrast to results obtained in the nematode where phenotypes could be obtained when the sense and antisense strands were injected separately (A. Fire et al., Nature 391, 806-810 (1998)).

Figure 12:
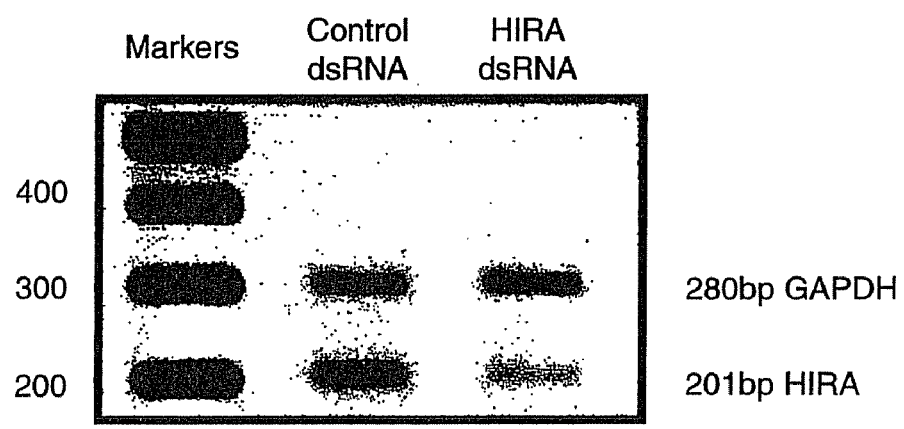
FIG. 12 shows the effect of HirA double-stranded RNA on the expression of HirA in explanted chick cardiac neural crest tissue.

None of the control treatments, i.e., single strand sense or antisense, or control ds RNA showed any phenotypes at any concentrations that were tested. The only phenotypes we observed were after injection of Zf-T or Pax6.1 double-stranded RNA, and these phenotypes specifically matched the treatment. In this regard double-stranded RNA targeted to Pax6.1 affected head and eye development with no apparent effect on tail development (FIG. 12). On the other hand Zf-T ds RNA affected tail development without any apparent effect on the head or eye (FIG. 4). Thus this treatment does not behave like a non-specific, toxic effect which would be expected to yield similar phenotypes regardless of the double-stranded RNA injected.

GFP, a reporter gene encoding a protein that fluoresces when exposed to ultraviolet light, allows promoter activity to be monitored in living embryos throughout development. Using this reporter gene, it has been possible to identify promoter regions that regulate gene expression in the zebrafish notochord, sympathetic neurons, and hematopoetic lineages. We microinjected single-cell embryos with a plasmid vector containing GFP regulated by a promoter that drives ubiquitous expression during early development. We found that co-injection of double-stranded RNA specifically targeted to GFP suppressed expression of this reporter gene in well over 95% of the embryos injected with the plasmid vector.

While it might at first be thought that the GFP plasmid vector would be a good marker for the distribution of double-stranded RNA, the differences in these two nucleotides might predict great differences in their processing by the embryo for two reasons. The GFP plasmid is approximately 5000 base pairs of deoxyribonucleotides while the double-stranded RNA is composed of ribonucleotides and it is a very short piece by comparison (around 200 base pairs). Data from *C. elegans* (Montgomery et al., 1998) and our own observations indicate that the double-stranded RNA has much freer access to the cell from the extracellular matrix than does the GFP expressing plasmid. Whether this is because of the difference in nucleotide composition or size is not known.

The injection of Zf-T double-stranded RNA into single cell zebrafish embryos resulted in greatly diminished expression of the Zf-T as monitored by in situ hybridization and semi-quantitative RT-PCR, and resulted in phenotypes very similar to those found in ntl zebrafish embryos. Our in situs of ntl are shown at 9 hours. Most of the published ntl in situs show embryos at 11 hours or later and the signal is stronger than what we have shown in FIG. 4. However, it seems clear from this figure that the ntl expression is completely absent after the double-stranded RNA injection and correlates perfectly with the phenotypes of the older embryos. This visual result is substantiated by semiquantitative RT-PCR showing that the Zf-T message is reduced to 70% of control level. It should be emphasized that semiquantitative RT-PCR was done using pooled zebrafish embryos and the message levels would represent the whole range of phenotypes shown in FIG. 9. Thus a 70% reduction in message level seems quite reasonable.

Not only is the phenotype grossly similar to ntl, it is quite specific. In more than 70% of the embryos injected with the double-stranded Zf-T RNA, the notochord was absent or greatly diminished. Twenty-one percent of the embryos examined had no notochord. The somites in these embryos also lacked the characteristic chevron appearance observed in wild type embryos, similar to the ntl mutant. The ntl phenotype can be distinguished from that of another tailless phenotype seen in the floating head mutant by the lack of fusion of the somites across the midline. Embryos injected with Zf-T double-stranded RNA did not show fusion of the somites across the midline providing a differential diagnosis for the ntl versus the similar floating head phenotype.

That these phenotypic characteristics were due to specific attenuation of Zf-T expression was supported by in situ hybridizations showing altered expression patterns of shh and flh. Zf-T expression was greatly diminished in 30-50% and absent in 20% of the embryos injected with the Zf-T double-stranded RNA. Expression of shh and flh were also altered in the zebrafish midline in these embryos in a manner similar to that found in the ntl mutant. The expression patterns of these genes appeared to be identical to those found in the ntl mutant in approximately 25% of the microinjected embryos that were examined. The expression patterns were altered in a similar, but less complete manner, in more than 60% of the microinjected embryos.

Twenty-five percent of zebrafish embryos that were injected with Zf-Pax6.1 double-stranded RNA had underdeveloped heads and absent or greatly diminished eyes. In situ hybridizations confirmed that Pax6.1 expression was greatly diminished in more than 90% of the embryos injected with Zf-Pax6.1 double-stranded RNA. Pax6.1 expression was not affected in embryos injected with a control double-stranded RNA. The relatively low occurrence of phenotypes in embryos injected with Pax6.1 double-stranded RNA may be due to functional redundancy of the closely related Pax6.2, which is expressed in overlapping regions of the zebrafish embryo. Interestingly, simultaneous injection of double-stranded RNA targeted to Pax6.1 and ntl gives a very clear compound phenotype that is quite distinct from the phenotypes resulting from injection of either double-stranded RNA separately. We believe that this data along with that from simultaneous injection of GFP expression vector with Zf-T double-stranded RNA in which the effect appeared completely independent forms a compelling argument to support the idea that treatment with double-stranded RNA causes a relatively specific cellular response.

Finally, it is known that certain types of double-stranded RNA, such as mismatched or polyI/polyC RNA, can be toxic at high concentrations in eukaryotic animals (M. Kumar et al., *Microbiol. Mol. Biol. Rev.* 62, 1415-1434 (1998)). Although double-stranded RNA can induce interferon-α/β in non-immune cells, this toxicity is primarily due to an immune system response mediated through interferon production in response to viral infections. Immune system or interferon-α/β-mediated toxicity is very unlikely to play any role in generating the phenotypes we have observed. First, the phenotypes that we have generated can be observed in 24 hour embryos, long before the zebrafish immune system has been established. The thymus primordium appears in the zebrafish at approximately 54 hours, but does not enlarge significantly until 30 hours later. Rag1 and Rag2 expression cannot be detected until day 4, indicating a lack of mature T cells in the zebrafish until that time. Second, the amount of double-stranded RNA that was used to generate the phenotypes is much less than is necessary to cause this interferon-mediated cell toxicity (M. Kumar et al., *Microbiol. Mol. Biol. Rev.* 62, 1415-1434 (1998)). We have also found that polyI/polyC RNA can be toxic both in cultured 3T3 cells and in microinjected embryos. However, none of the ten double-stranded RNAs that we have so far examined elicit a toxic effect in vitro or in vivo. Third, the phenotypes that have been generated for each gene under study differ substantially from one another and are specifically related to the gene that was targeted. Finally, injection of control double-stranded RNA at the same concentrations does not cause a detectable deviation from the wild type expression levels or phenotype.

In summary, these results show that double-stranded RNA can efficiently disrupt gene activity in zebrafish. This inhibitory activity appears to be specific to the targeted gene. Non-specific double-stranded RNA had no apparent phenotypic effect. We have also shown that multiple genes can be simultaneously targeted.

Example II

Double-Stranded RNA Injection Blocks Gene Expression in Explanted Cardiac Neural Crest Tissue Attenuated expression of HirA (GenBank accession number X99375) is known to be associated with increased persistent truncus arteriosus (PTA). Double-stranded RNA was generated from a chick HirA cDNA fragment in essentially the same manner as described for zebrafish in Example I. The upstream primer was 5' TCTGCACCAGCATTAGCACT (SEQ ID NO:19) and the downstream primer was 5' TGCT-GTGAGAATTCGACTGG (SEQ ID NO:20) yielding a 201 base pair product representing positions 2095 to 2295 of the HirA cDNA sequence.

Explanted chick neural crest was incubated for 1.5 hours with HirA dsRNA or nonspecific dsRNA (control ntl dsRNA) in DMEM. The concentration of double-stranded RNA applied was approximately $10^6$ molecules per nanoliter. Following exposure to the double-stranded RNA each piece of tissue was washed in PBS prior to placing the tissue into culture.

FIG. 12 shows that double-stranded HirA RNA effectively silences expression of HirA in cardiac neural crest cell culture. Using RT-PCR as described in Example I, it was determined that the HirA message was decreased by 58%. This inhibitory activity appears to be specific to the targeted gene. Non-specific double-stranded RNA had no apparent effect.

Example III

Double-Stranded RNA Injection Blocks Gene Expression in Mammalian Cell Culture

Double-stranded GFP RNA was prepared as described in Example I. Murine NIH/3T3 cells were transfected with pEGFP-N1 and double stranded GFP RNA using a standard transfection procedure. First, murine NIH/3T3 cells (~$2 \times 10^8$ per well) were seeded in a six-well tissue culture plate in 2 ml of DMEM with 10% FBS. The cells were then incubated at 37° C. in a $CO_2$ incubator until they were about 70-80% confluent (i.e., 18-24 hours).

For each transfection, Solution A was made by diluting 1 μg of pEGFP-N1 and 0.5-1 μg of double stranded GFP RNA into 100 μl serum-free medium (OPTI-MEM® 1 Reduced Serum Medium, GIBCO BRL Cat. No. 320-1985), and Solution B was made by diluting 3-12 μl of LIPOFECTAMINE Reagent into 100 μl serum-free medium. For one control experiment, Solution A contained the plasmid pEGFP-N1 but no double stranded RNA; for another, Solution A contained the plasmid pEGFP-N1 a control double-stranded ntl RNA. The two solutions were combined, mixed gently, and incubated at room temperature for 30 minutes. The cells were washed once with 2 ml of serum-free DMEM. For each transfection, 0.8 ml of serum-free DMEM was added to each tube containing the lipid-DNA complexes. The tubes were mixed gently and the diluted complex solution was overlayed onto the washed cells. The cells were incubated for 5 hours at 37° C. in a $CO_2$ incubator. DMEM (1 mL) was added with 20% FBS without removing the transfection mixture. Medium was replaced at 18-24 hours following the start of transfection. Cell extracts were assayed for GFP activity 24-72 hours after the start of transfection. GFP expression was monitored by fluorescence microscopy.

Figure 13:
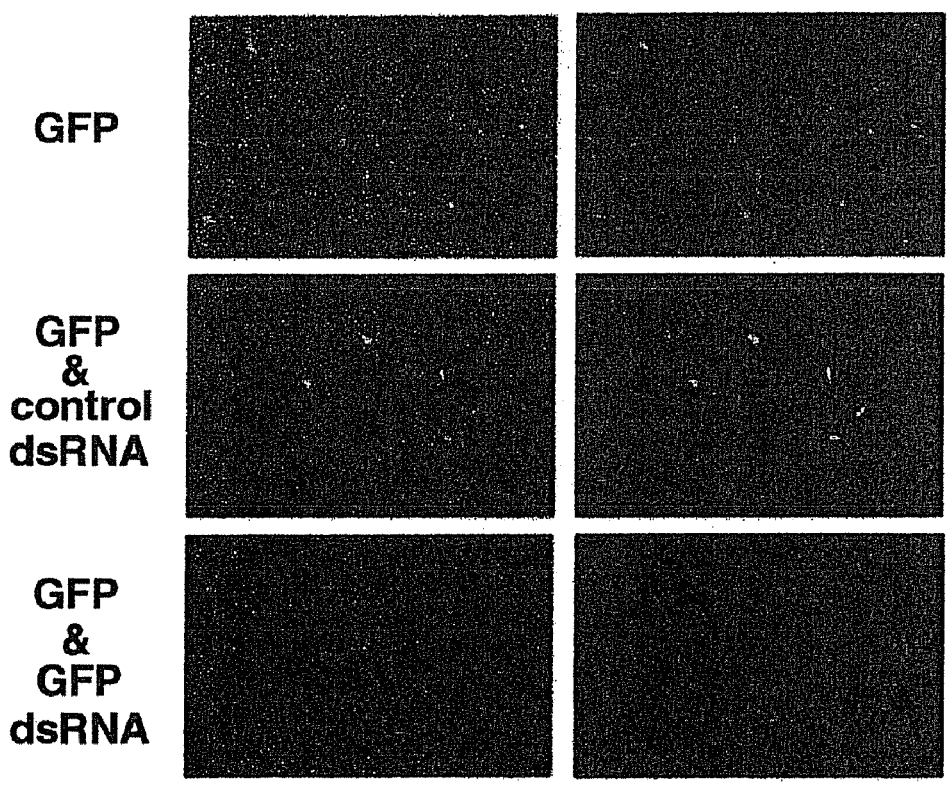
FIG. 13 shows the effect of GFP double-stranded RNA injection on transient expression of GFP in murine cell culture.

As shown in FIG. 13, transformed cells incubated with double-stranded GFP RNA molecules exhibited substantially reduced GFP expression. In contrast, transformed cells incubated with control dsRNA showed no apparent change in GFP expression.

The complete disclosure of all patents, patent applications, and publications, and electronically available material (e.g., GenBank amino acid and nucleotide sequence submissions) cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:

1. A method for attenuating the expression of a target gene in an embryonic zebrafish cell in vivo comprising supplying the cell with a double stranded RNA in an amount sufficient to specifically attenuate expression of the target gene, wherein one of the strands of the double stranded RNA is capable of hybridizing to the target gene in vitro in 400 mM NaCl, 40 mM PIPES pH 6.4, and 1 mM EDTA, at 50° C., and provided that, when the double stranded RNA is supplied to the cell by delivery to the cell of double stranded RNA, the double stranded RNA is formed from single-stranded RNA that is purified in the absence of phenol or chloroform.

2. The method of claim 1, wherein the target gene is an endogenous gene.

3. The method of claim 1, wherein the target gene is a foreign gene.

4. The method of claim 1, wherein the target gene is a chromosomal gene.

5. The method of claim 1, wherein the target gene is an extrachromosomal gene.

6. The method of claim 1, wherein the target gene is from a pathogen capable of infecting the embryonic zebrafish cell.

7. The method of claim 6, wherein the pathogen is selected from the group consisting of a virus, bacterium, fungus or protozoan.

8. The method of claim 1, wherein the double stranded RNA comprises a nucleotide sequence that is complementary to the nucleotide sequence of at least a portion of the target gene.

9. The method of claim 1, wherein the double stranded RNA comprises a nucleotide sequence that is complementary to a region of at least about 25 bases of the target gene.

10. The method of claim 1, wherein the double stranded RNA is supplied in an amount sufficient to completely inhibit expression of the target gene.

11. The method of claim 1 in which the double stranded RNA comprises a single strand comprising self-complementary portions.

12. The method of claim 1 in which the double stranded RNA comprises two separate complementary strands.

13. The method of claim 1, wherein the embryonic zebrafish cell is supplied with the double stranded RNA using microinjection.

14. The method of claim 1, wherein supplying the double stranded RNA to the embryonic zebrafish cell comprises delivering double-stranded RNA to the embryonic zebrafish cell, and wherein the double stranded RNA is treated with RNAse prior to delivery to the embryonic zebrafish cell.

15. The method of claim 1, wherein supplying the double stranded RNA to the embryonic zebrafish cell comprises delivering double stranded RNA to the embryonic zebrafish cell, the method further comprising, prior to delivering the double stranded RNA to the embryonic zebrafish cell, annealing two complementary single stranded RNAs to yield the double stranded RNA.

16. The method of claim 15, wherein the single stranded RNAs are annealed in the presence of potassium chloride.

17. The method of claim 1, wherein the function of the target gene is unknown.

18. The method of claim 1 further comprising introducing into the embryonic zebrafish cell a second double stranded RNA in an amount sufficient to attenuate expression of a second target gene, wherein one of the strands of the second double stranded RNA is capable of hybridizing to the second target gene in vitro in 400 mM NaCl, 40 mM PIPES pH 6.4, and 1 mM EDTA, at 50° C.

19. The method of claim 1 comprising introducing into the embryonic zebrafish cell multiple double stranded RNAs in an amount sufficient to attenuate expression of multiple target genes, wherein one strand of each double stranded RNA is capable of hybridizing to the corresponding target gene in vitro in 400 mM NaCl, 40 mM PIPES pH 6.4, and 1 mM EDTA, at 50° C.

20. The method of claim 1 further comprising identifying a phenotypic change in the zebrafish associated with attenuated expression of the target gene.

21. A method for attenuating the expression of a target gene in an embryonic zebrafish cell comprising:
   annealing two complementary single stranded RNAs in the presence of potassium chloride to yield double stranded RNA;
   contacting the double stranded RNA with RNAse to purify the double stranded RNA by removing single stranded RNA; and
   introducing the purified double stranded RNA into the cell in an amount sufficient to specifically attenuate expression of the target gene;
   wherein one of the strands of the double stranded RNA is capable of hybridizing to the target gene in vitro in 400 mM NaCl, 40 mM PIPES pH 6.4, and 1 mM EDTA, at 50° C., and wherein the double stranded RNA is formed from single-stranded RNA that is purified in the absence of phenol or chloroform.

22. The method of claim 1, wherein one of the strands of the double stranded RNA is capable of hybridizing to the target gene in vitro in 400 mM NaCl, 40 mM PIPES pH 6.4, and 1 mM EDTA, at 70° C.

23. A method for attenuating the expression of a target gene in an embryonic zebrafish cell in vivo comprising delivering a double stranded RNA to the embryonic zebrafish cell in an amount sufficient to specifically attenuate expression of the target gene, wherein the double stranded RNA comprises a nucleotide sequence that is complementary to a region of at least 25 nucleotides of the target gene, and wherein the double stranded RNA is formed from single-stranded RNA that is purified in the absence of phenol or chloroform.

24. The method of claim 23, wherein the target gene is associated with a disease.

25. The method of claim 23, wherein the target gene is associated with a disease from a pathogen.

26. The method of claim 1, wherein the double stranded RNA is supplied to the embryonic zebrafish cell by delivering to the cell a DNA encoding the double stranded RNA.

27. The method of claim 1, wherein the double stranded RNA has a length of less than about 200 bases.

28. The method of claim 11, wherein the double stranded RNA comprises a nucleotide sequence that is complementary to a region of at least about 25 bases of the target gene.

29. The method of claim 12, wherein the double stranded RNA comprises a nucleotide sequence that is complementary to a region of at least about 25 bases of the target gene.

30. A method for attenuating the expression of a target gene in an embryonic fish cell in vivo comprising supplying the cell with a double stranded RNA in an amount sufficient to specifically attenuate expression of the target gene, wherein one of the strands of the double stranded RNA is capable of hybridizing to the target gene in vitro in 400 mM NaCl, 40 mM PIPES pH 6.4, and 1 mM EDTA, at 50° C., and provided that, when the double stranded RNA is supplied to the cell by delivery to the cell of double stranded RNA, the double stranded RNA is formed from single-stranded RNA that is purified in the absence of phenol or chloroform.

* * * * *